United States Patent
Olson et al.

(10) Patent No.: US 9,072,765 B2
(45) Date of Patent: Jul. 7, 2015

(54) IDENTIFICATION OF MICRO-RNAS INVOLVED IN POST-MYOCARDIAL INFARCTION REMODELING AND HEART FAILURE

(75) Inventors: Eric N. Olson, Dallas, TX (US); Eva van Rooij, Boulder, CO (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/321,756

(22) PCT Filed: May 20, 2010

(86) PCT No.: PCT/US2010/035642
§ 371 (c)(1),
(2), (4) Date: Feb. 14, 2012

(87) PCT Pub. No.: WO2010/135570
PCT Pub. Date: Nov. 25, 2010

(65) Prior Publication Data
US 2012/0165392 A1   Jun. 28, 2012

Related U.S. Application Data

(60) Provisional application No. 61/179,775, filed on May 20, 2009.

(51) Int. Cl.
*A61K 48/00* (2006.01)
*A61K 31/7105* (2006.01)
*A61K 31/7088* (2006.01)

(52) U.S. Cl.
CPC .......... *A61K 31/7105* (2013.01); *A61K 31/7088* (2013.01)

(58) Field of Classification Search
None
See application file for complete search history.

(56) References Cited

U.S. PATENT DOCUMENTS

2008/0050744 A1   2/2008   Brown et al.
2010/0010073 A1   1/2010   Thum et al.

FOREIGN PATENT DOCUMENTS

WO   WO 2008/043521 A2   4/2008

OTHER PUBLICATIONS

Young, "International Search Report and Written Opinion," 6 pages, International Application No. PCT/US2010/035642, U.S. Patent Office, Alexandria, VA, mailed Aug. 30, 2010.

*Primary Examiner* — Kimberly Chong
(74) *Attorney, Agent, or Firm* — Parker Highlander PLLC

(57) ABSTRACT

The present invention relates to the identification of miRNAs that are involved in heart failure and the process of post-myocardial infarction remodeling in heart tissue. Modulation of these identified miRNAs as a treatment for myocardial infarction, cardiac remodelling, and heart failure is described.

17 Claims, 5 Drawing Sheets

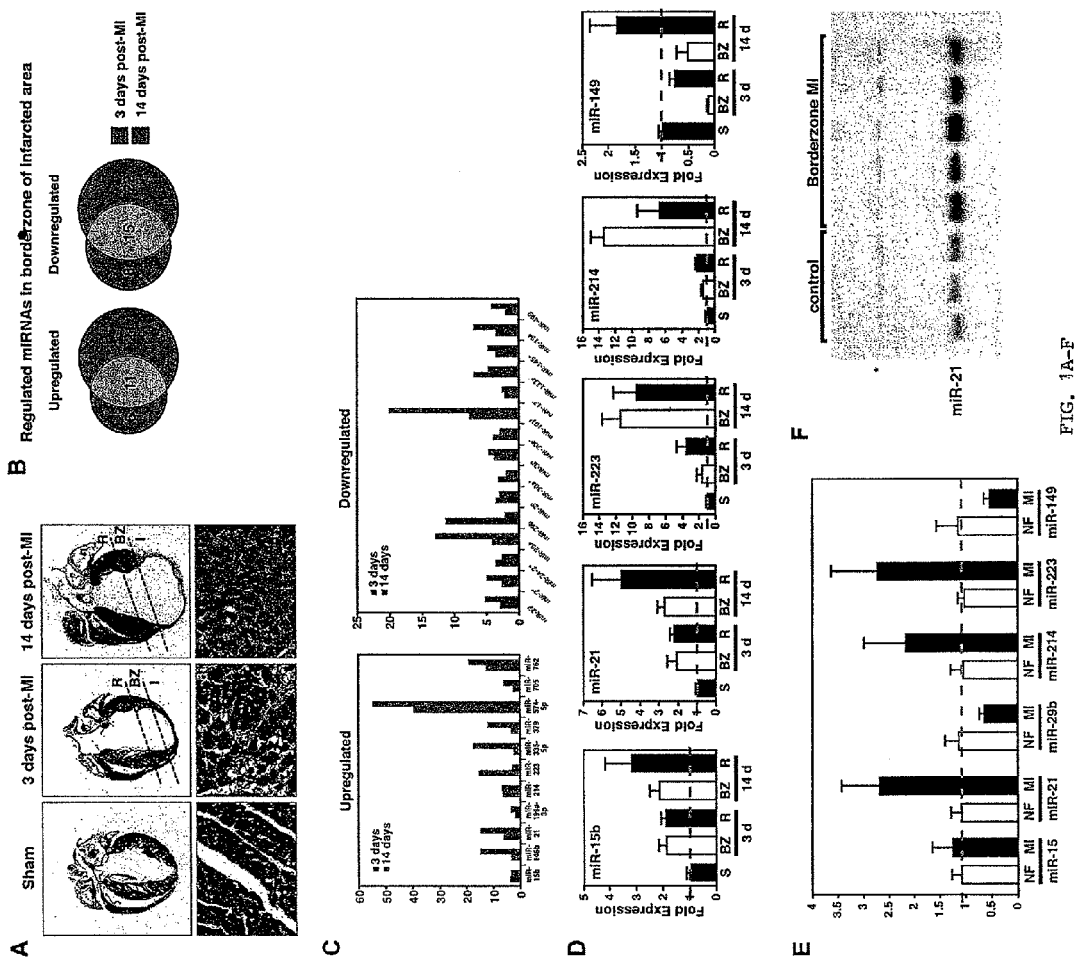
FIG. 1A-F

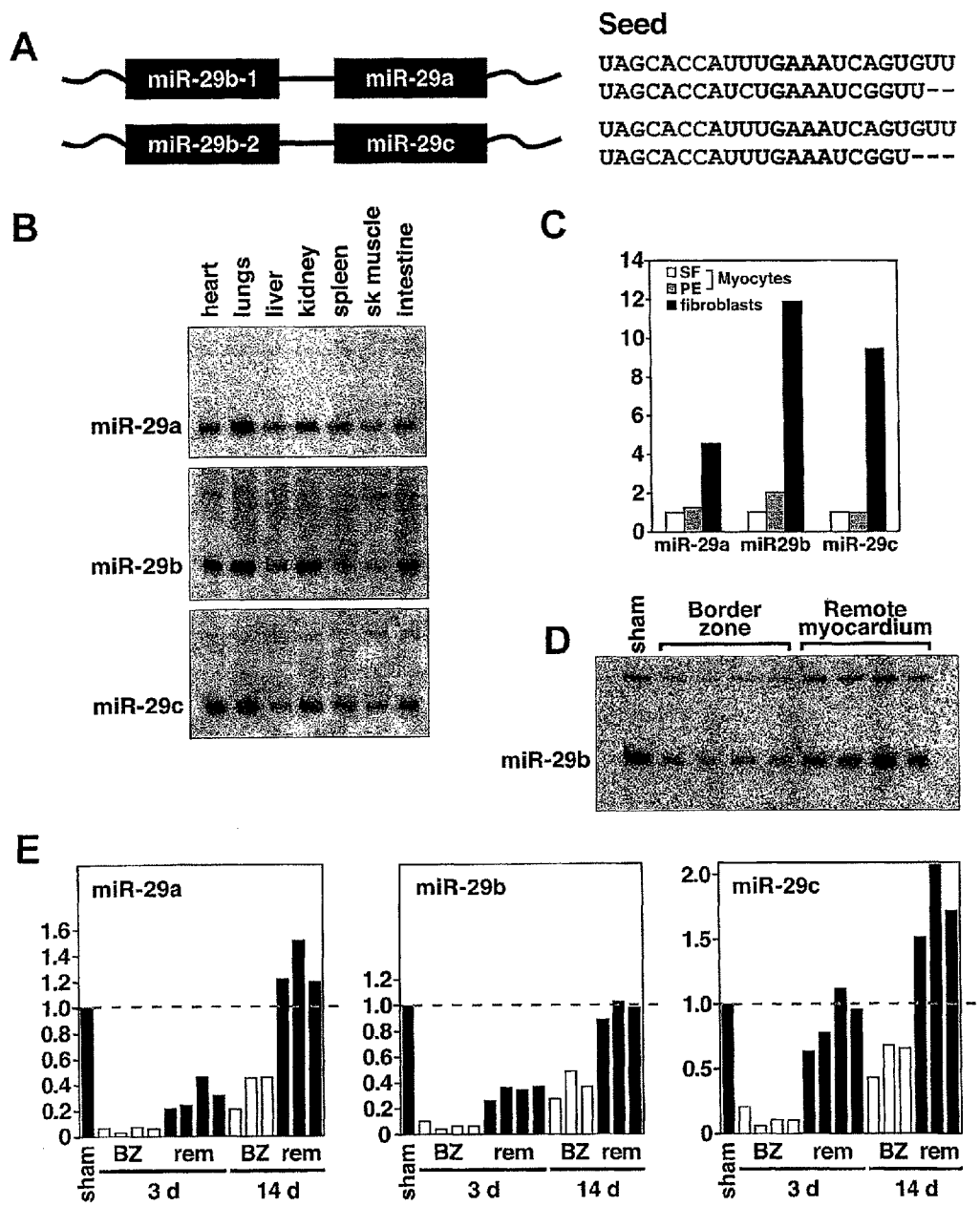
FIG. 2A-E

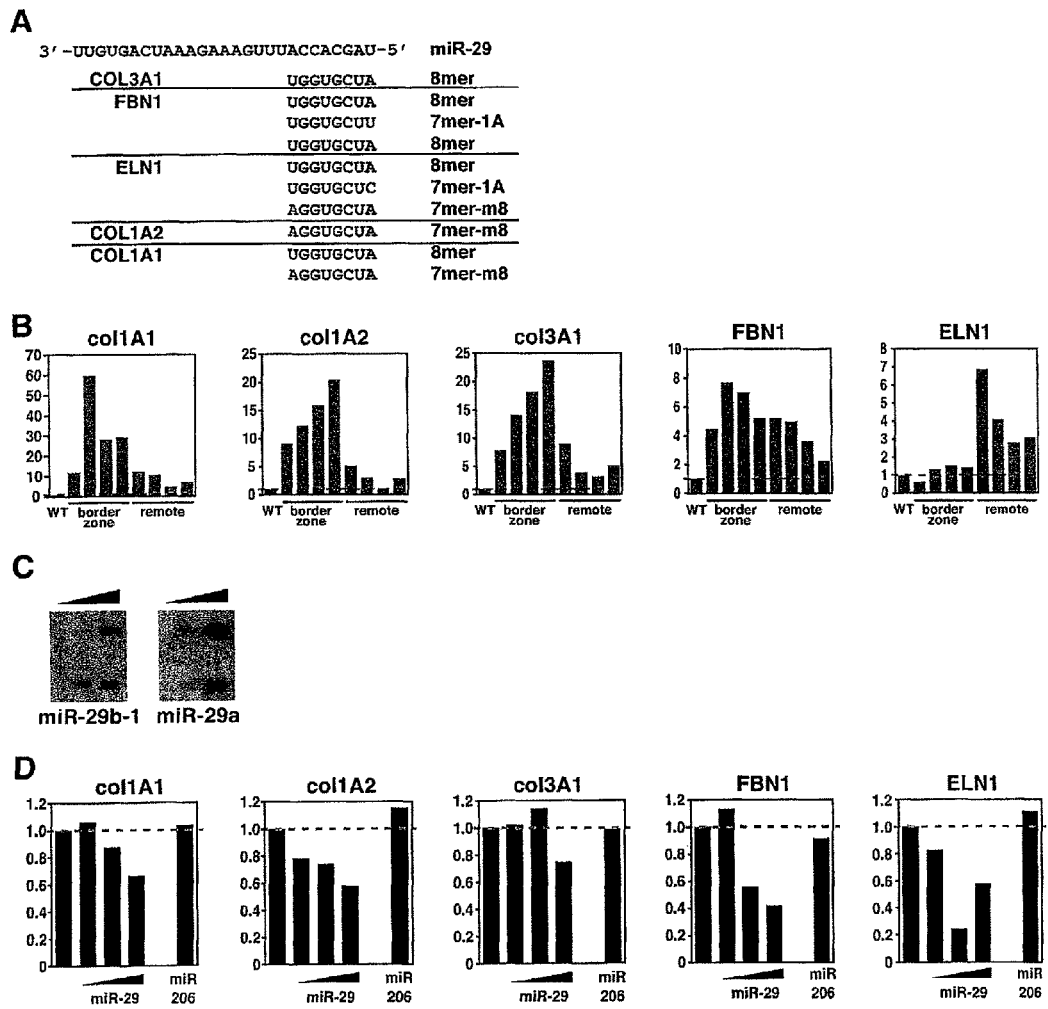
FIG. 3A-D

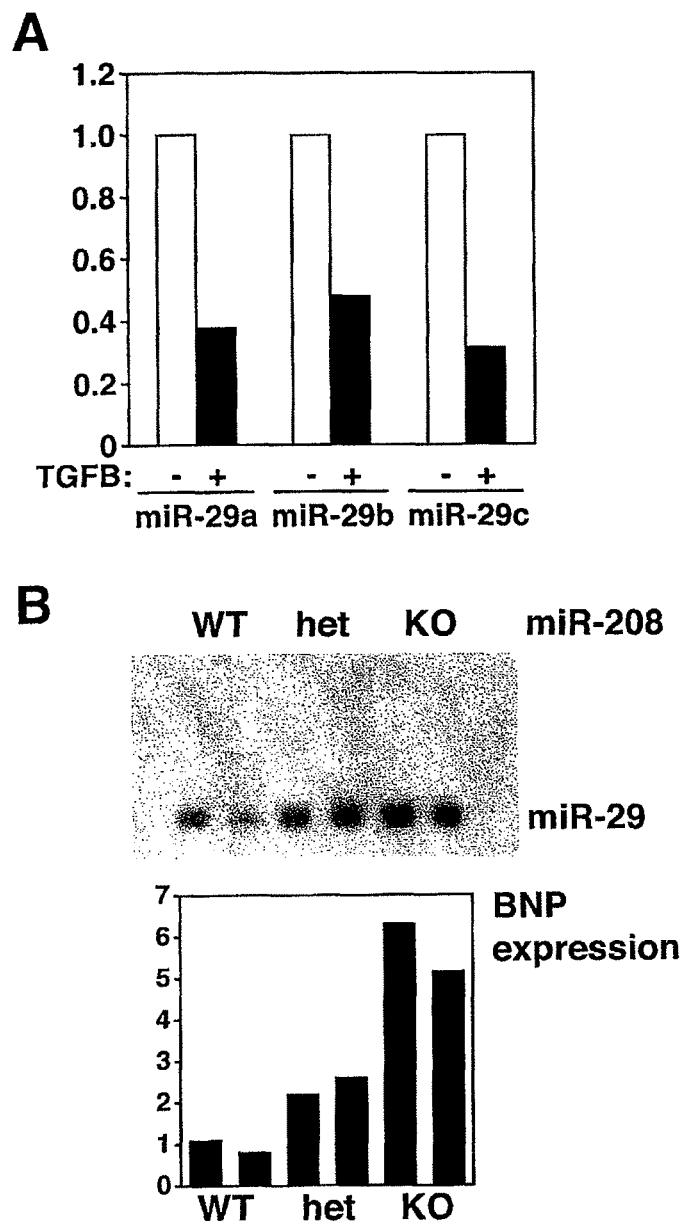
FIG. 4A-B

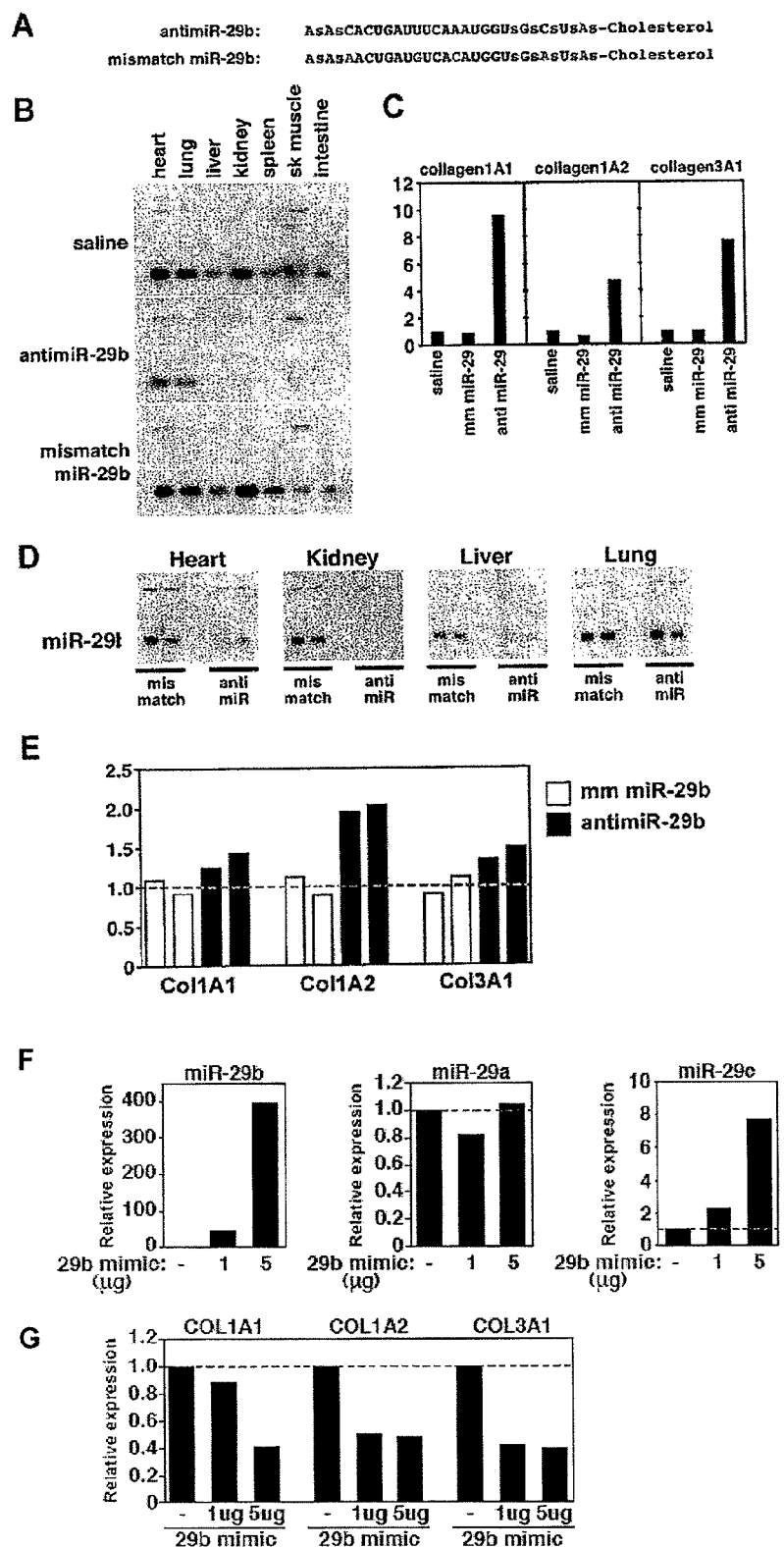
FIGURE 5A-G

SEQUENCE LISTING

```
<160> NUMBER OF SEQ ID NOS: 63

<210> SEQ ID NO 1
<211> LENGTH: 22
<212> TYPE: RNA
<213> ORGANISM: Homo sapiens

<400> SEQUENCE: 1
ugagguagua gguuguauag uu                                              22

<210> SEQ ID NO 2
<211> LENGTH: 22
<212> TYPE: RNA
<213> ORGANISM: Homo sapiens

<400> SEQUENCE: 2
ugagguagua gguugugugg uu                                              22

<210> SEQ ID NO 3
<211> LENGTH: 22
<212> TYPE: RNA
<213> ORGANISM: Homo sapiens

<400> SEQUENCE: 3
ugagguagua gguuguaugg uu                                              22

<210> SEQ ID NO 4
<211> LENGTH: 22
<212> TYPE: RNA
<213> ORGANISM: Homo sapiens

<400> SEQUENCE: 4
agagguagua gguugcauag uu                                              22

<210> SEQ ID NO 5
<211> LENGTH: 22
<212> TYPE: RNA
<213> ORGANISM: Homo sapiens

<400> SEQUENCE: 5
ugagguagga gguuguauag uu                                              22

<210> SEQ ID NO 6
<211> LENGTH: 22
<212> TYPE: RNA
<213> ORGANISM: Homo sapiens

<400> SEQUENCE: 6
ugagguagua gauuguauag uu                                              22

<210> SEQ ID NO 7
<211> LENGTH: 22
<212> TYPE: RNA
<213> ORGANISM: Homo sapiens

<400> SEQUENCE: 7
ugagguagua guuuguacag uu                                              22

<210> SEQ ID NO 8
<211> LENGTH: 22
<212> TYPE: RNA
<213> ORGANISM: Homo sapiens

<400> SEQUENCE: 8
```

```
ugagguagua guuugugcug uu                                        22

<210> SEQ ID NO 9
<211> LENGTH: 22
<212> TYPE: RNA
<213> ORGANISM: Homo sapiens

<400> SEQUENCE: 9
uagcagcaca ucaugguuua ca                                        22

<210> SEQ ID NO 10
<211> LENGTH: 22
<212> TYPE: RNA
<213> ORGANISM: Homo sapiens

<400> SEQUENCE: 10
uagcuuauca gacugauguu ga                                        22

<210> SEQ ID NO 11
<211> LENGTH: 23
<212> TYPE: RNA
<213> ORGANISM: Homo sapiens

<400> SEQUENCE: 11
cccaguguuc agacuaccug uuc                                       23

<210> SEQ ID NO 12
<211> LENGTH: 23
<212> TYPE: RNA
<213> ORGANISM: Homo sapiens

<400> SEQUENCE: 12
cccaguguuu agacuaucug uuc                                       23

<210> SEQ ID NO 13
<211> LENGTH: 22
<212> TYPE: RNA
<213> ORGANISM: Homo sapiens

<400> SEQUENCE: 13
acaguagucu gcacauuggu ua                                        22

<210> SEQ ID NO 14
<211> LENGTH: 22
<212> TYPE: RNA
<213> ORGANISM: Homo sapiens

<400> SEQUENCE: 14
acagcaggca cagacaggca gu                                        22

<210> SEQ ID NO 15
<211> LENGTH: 23
<212> TYPE: RNA
<213> ORGANISM: Homo sapiens

<400> SEQUENCE: 15
uacccuguag auccgaauuu gug                                       23

<210> SEQ ID NO 16
<211> LENGTH: 23
<212> TYPE: RNA
<213> ORGANISM: Homo sapiens
```

```
<400> SEQUENCE: 16
uacccuguag aaccgaauuu gug                                        23

<210> SEQ ID NO 17
<211> LENGTH: 22
<212> TYPE: RNA
<213> ORGANISM: Homo sapiens

<400> SEQUENCE: 17
uagcagcacg uaaauauugg cg                                         22

<210> SEQ ID NO 18
<211> LENGTH: 22
<212> TYPE: RNA
<213> ORGANISM: Homo sapiens

<400> SEQUENCE: 18
ugagaacuga auuccauggg uu                                         22

<210> SEQ ID NO 19
<211> LENGTH: 22
<212> TYPE: RNA
<213> ORGANISM: Homo sapiens

<400> SEQUENCE: 19
ugagaacuga auuccauagg cu                                         22

<210> SEQ ID NO 20
<211> LENGTH: 22
<212> TYPE: RNA
<213> ORGANISM: Homo sapiens

<400> SEQUENCE: 20
ugcccugugg acucaguucu gg                                         22

<210> SEQ ID NO 21
<211> LENGTH: 23
<212> TYPE: RNA
<213> ORGANISM: Homo sapiens

<400> SEQUENCE: 21
agcuacauug ucugcugggu uuc                                        23

<210> SEQ ID NO 22
<211> LENGTH: 21
<212> TYPE: RNA
<213> ORGANISM: Homo sapiens

<400> SEQUENCE: 22
agcuacaucu ggcuacuggg u                                          21

<210> SEQ ID NO 23
<211> LENGTH: 21
<212> TYPE: RNA
<213> ORGANISM: Homo sapiens

<400> SEQUENCE: 23
cagcagcaca cuguggguuug u                                         21

<210> SEQ ID NO 24
<211> LENGTH: 23
<212> TYPE: RNA
<213> ORGANISM: Homo sapiens
```

```
<400> SEQUENCE: 24
uaaagugcuu auagugcagg uag                                            23

<210> SEQ ID NO 25
<211> LENGTH: 23
<212> TYPE: RNA
<213> ORGANISM: Homo sapiens

<400> SEQUENCE: 25
caaagugcuc auagugcagg uag                                            23

<210> SEQ ID NO 26
<211> LENGTH: 23
<212> TYPE: RNA
<213> ORGANISM: Homo sapiens

<400> SEQUENCE: 26
caaagugcug uucgugcagg uag                                            23

<210> SEQ ID NO 27
<211> LENGTH: 21
<212> TYPE: RNA
<213> ORGANISM: Homo sapiens

<400> SEQUENCE: 27
uacaguacug ugauaacuga a                                              21

<210> SEQ ID NO 28
<211> LENGTH: 22
<212> TYPE: RNA
<213> ORGANISM: Homo sapiens

<400> SEQUENCE: 28
ucguaccgug aguaauaaug cg                                             22

<210> SEQ ID NO 29
<211> LENGTH: 22
<212> TYPE: RNA
<213> ORGANISM: Homo sapiens

<400> SEQUENCE: 29
uguaaacauc cucgacugga ag                                             22

<210> SEQ ID NO 30
<211> LENGTH: 22
<212> TYPE: RNA
<213> ORGANISM: Homo sapiens

<400> SEQUENCE: 30
uguaaacauc cuacacucag cu                                             22

<210> SEQ ID NO 31
<211> LENGTH: 23
<212> TYPE: RNA
<213> ORGANISM: Homo sapiens

<400> SEQUENCE: 31
uguaaacauc cuacacucuc agc                                            23

<210> SEQ ID NO 32
<211> LENGTH: 22
<212> TYPE: RNA
```

```
<213> ORGANISM: Homo sapiens

<400> SEQUENCE: 32
uguaaacauc cccgacugga ag                                          22

<210> SEQ ID NO 33
<211> LENGTH: 22
<212> TYPE: RNA
<213> ORGANISM: Homo sapiens

<400> SEQUENCE: 33
uguaaacauc cuugacugga ag                                          22

<210> SEQ ID NO 34
<211> LENGTH: 21
<212> TYPE: RNA
<213> ORGANISM: Homo sapiens

<400> SEQUENCE: 34
ugagaugaag cacuguagcu c                                           21

<210> SEQ ID NO 35
<211> LENGTH: 23
<212> TYPE: RNA
<213> ORGANISM: Homo sapiens

<400> SEQUENCE: 35
guccaguuuu cccaggaauc ccu                                         23

<210> SEQ ID NO 36
<211> LENGTH: 22
<212> TYPE: RNA
<213> ORGANISM: Homo sapiens

<400> SEQUENCE: 36
ucucccaacc cuuguaccag ug                                          22

<210> SEQ ID NO 37
<211> LENGTH: 22
<212> TYPE: RNA
<213> ORGANISM: Homo sapiens

<400> SEQUENCE: 37
uagcaccauc ugaaaucggu ua                                          22

<210> SEQ ID NO 38
<211> LENGTH: 23
<212> TYPE: RNA
<213> ORGANISM: Homo sapiens

<400> SEQUENCE: 38
uagcaccauu ugaaaucagu guu                                         23

<210> SEQ ID NO 39
<211> LENGTH: 22
<212> TYPE: RNA
<213> ORGANISM: Homo sapiens

<400> SEQUENCE: 39
uagcaccauu ugaaaucggu ua                                          22

<210> SEQ ID NO 40
<211> LENGTH: 22
```

<212> TYPE: RNA
<213> ORGANISM: Homo sapiens

<400> SEQUENCE: 40
uggcaguguc uuagcugguu gu                                              22

<210> SEQ ID NO 41
<211> LENGTH: 23
<212> TYPE: RNA
<213> ORGANISM: Homo sapiens

<400> SEQUENCE: 41
aggcagugua guuagcugau ugc                                             23

<210> SEQ ID NO 42
<211> LENGTH: 22
<212> TYPE: RNA
<213> ORGANISM: Homo sapiens

<400> SEQUENCE: 42
aaucacuaac cacacggcca gg                                              22

<210> SEQ ID NO 43
<211> LENGTH: 23
<212> TYPE: RNA
<213> ORGANISM: Homo sapiens

<400> SEQUENCE: 43
ugagugugug ugugugagug ugu                                             23

<210> SEQ ID NO 44
<211> LENGTH: 22
<212> TYPE: RNA
<213> ORGANISM: Homo sapiens

<400> SEQUENCE: 44
cacgcucaug cacacaccca ca                                              22

<210> SEQ ID NO 45
<211> LENGTH: 22
<212> TYPE: RNA
<213> ORGANISM: Homo sapiens

<400> SEQUENCE: 45
aaaccguuac cauuacugag uu                                              22

<210> SEQ ID NO 46
<211> LENGTH: 21
<212> TYPE: RNA
<213> ORGANISM: Homo sapiens

<400> SEQUENCE: 46
uuaagacuug cagugauguu u                                               21

<210> SEQ ID NO 47
<211> LENGTH: 22
<212> TYPE: RNA
<213> ORGANISM: Homo sapiens

<400> SEQUENCE: 47
aacccguaga uccgaacuug ug                                              22

<210> SEQ ID NO 48

```
<211> LENGTH: 21
<212> TYPE: RNA
<213> ORGANISM: Homo sapiens

<400> SEQUENCE: 48
acuggacuug gagucagaag g                                              21

<210> SEQ ID NO 49
<211> LENGTH: 22
<212> TYPE: RNA
<213> ORGANISM: Homo sapiens

<400> SEQUENCE: 49
uggcucaguu cagcaggaac ag                                             22

<210> SEQ ID NO 50
<211> LENGTH: 21
<212> TYPE: RNA
<213> ORGANISM: Homo sapiens

<400> SEQUENCE: 50
ugguagacua uggaacguag g                                              21

<210> SEQ ID NO 51
<211> LENGTH: 22
<212> TYPE: RNA
<213> ORGANISM: Homo sapiens

<400> SEQUENCE: 51
ggggcugggg ccggggccga gc                                             22

<210> SEQ ID NO 52
<211> LENGTH: 23
<212> TYPE: RNA
<213> ORGANISM: Homo sapiens

<400> SEQUENCE: 52
ucaagagcaa uaacgaaaaa ugu                                            23

<210> SEQ ID NO 53
<211> LENGTH: 22
<212> TYPE: RNA
<213> ORGANISM: Homo sapiens

<400> SEQUENCE: 53
gggacccagg gagagacgua ag                                             22

<210> SEQ ID NO 54
<211> LENGTH: 23
<212> TYPE: RNA
<213> ORGANISM: Homo sapiens

<400> SEQUENCE: 54
ucuggcuccg ugucuucacu ccc                                            23

<210> SEQ ID NO 55
<211> LENGTH: 21
<212> TYPE: RNA
<213> ORGANISM: Homo sapiens

<400> SEQUENCE: 55
uugugcuuga ucuaaccaug u                                              21
```

```
<210> SEQ ID NO 56
<211> LENGTH: 23
<212> TYPE: RNA
<213> ORGANISM: Homo sapiens

<400> SEQUENCE: 56
aacauucaac gcugucggug agu                                              23

<210> SEQ ID NO 57
<211> LENGTH: 23
<212> TYPE: RNA
<213> ORGANISM: Homo sapiens

<400> SEQUENCE: 57
aacauucauu gcugucggug ggu                                              23

<210> SEQ ID NO 58
<211> LENGTH: 22
<212> TYPE: RNA
<213> ORGANISM: Homo sapiens

<400> SEQUENCE: 58
aacauucaac cugucgguga gu                                               22

<210> SEQ ID NO 59
<211> LENGTH: 23
<212> TYPE: RNA
<213> ORGANISM: Homo sapiens

<400> SEQUENCE: 59
aacauucauu guugucggug ggu                                              23

<210> SEQ ID NO 60
<211> LENGTH: 22
<212> TYPE: RNA
<213> ORGANISM: Homo sapiens

<400> SEQUENCE: 60
aagcugccag uugaagaacu gu                                               22

<210> SEQ ID NO 61
<211> LENGTH: 22
<212> TYPE: RNA
<213> ORGANISM: Homo sapiens

<400> SEQUENCE: 61
uggagagaaa ggcaguuccu ga                                               22

<210> SEQ ID NO 62
<211> LENGTH: 23
<212> TYPE: RNA
<213> ORGANISM: Artificial Sequence
<220> FEATURE:
<223> OTHER INFORMATION: AntimiR-29b oligonucleotide
<220> FEATURE:
<221> NAME/KEY: misc_feature
<222> LOCATION: (1)..(23)
<223> OTHER INFORMATION: May be 2'-OMe modified
<220> FEATURE:
<221> NAME/KEY: misc_feature
<222> LOCATION: (1)..(2)
<223> OTHER INFORMATION: May be linked by a phosphorothioate bond
<220> FEATURE:
<221> NAME/KEY: misc_feature
<222> LOCATION: (20)..(23)
<223> OTHER INFORMATION: May be linked by a phosphorothioate bond
<220> FEATURE:
```

```
<221> NAME/KEY: misc_feature
<222> LOCATION: (23)..(23)
<223> OTHER INFORMATION: May have a 3' cholesterol moiety attached via a
      hydroxyprolinol linker

<400> SEQUENCE: 62
aacacugauu ucaaauggug cua                                             23

<210> SEQ ID NO 63
<211> LENGTH: 23
<212> TYPE: RNA
<213> ORGANISM: Artificial Sequence
<220> FEATURE:
<223> OTHER INFORMATION: Mismatch antimiR-29b oligonucleotide
<220> FEATURE:
<221> NAME/KEY: misc_feature
<222> LOCATION: (1)..(23)
<223> OTHER INFORMATION: May be 2'-OMe modified
<220> FEATURE:
<221> NAME/KEY: misc_feature
<222> LOCATION: (1)..(2)
<223> OTHER INFORMATION: May be linked by a phosphorothioate bond
<220> FEATURE:
<221> NAME/KEY: misc_feature
<222> LOCATION: (20)..(23)
<223> OTHER INFORMATION: May be linked by a phosphorothioate bond
<220> FEATURE:
<221> NAME/KEY: misc_feature
<222> LOCATION: (23)..(23)
<223> OTHER INFORMATION: May have a 3' cholesterol moiety attached via a
      hydroxyprolinol linker

<400> SEQUENCE: 63
aaaacugaug ucacauggug aua                                             23
```

IDENTIFICATION OF MICRO-RNAS INVOLVED IN POST-MYOCARDIAL INFARCTION REMODELING AND HEART FAILURE

CROSS-REFERENCE TO RELATED APPLICATIONS

This application is a national stage application of International Application No. PCT/US2010/035642, filed May 20, 2010, which claims the benefit of priority of U.S. Provisional Application No. 61/179,775, filed May 20, 2009, both of which are herein incorporated by reference in their entireties.

STATEMENT OF GOVERNMENT SUPPORT

This invention was made with grant support under grant no. HL53351-06 awarded by the National Institutes of Health. The government has certain rights in the invention.

FIELD OF THE INVENTION

The present invention relates generally to the fields of developmental biology, cardiology, pathology and molecular biology. More particularly, it concerns altered miRNA expression in post-myocardial infarction (post-MI) tissues and human heart failure samples. Manipulation of the expression of regulated miRNAs provides a novel therapeutic approach for treatment of myocardial infarction and heart failure.

BACKGROUND OF THE INVENTION

Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars. A particularly severe manifestation of heart disease is myocardial infarction. Myocardial infarction (MI), more commonly known as a heart attack, is a medical condition that occurs when the blood supply to a part of the heart is interrupted, most commonly due to rupture of a vulnerable plaque. The resulting ischemia or oxygen shortage causes damage and potential death of heart tissue. It is leading cause of death for both men and women throughout the world. In the United States alone, coronary heart disease is responsible for 1 in 5 deaths, and some 7,200,000 men and 6,000,000 women are living with some form of coronary heart disease. Of these, 1,200,000 people suffer a new or recurrent coronary attack every year, and about 40% of them die as a result of the attack. This means that roughly every 65 seconds, an American dies of a coronary event.

If impaired blood flow to the heart lasts long enough, it triggers an ischemic cascade, where the heart cells die from necrosis and a collagen scar forms in their place. Recent studies indicate that cell death from apoptosis also plays a role in the process of tissue damage subsequent to myocardial infarction. As a result, the patient's heart will be permanently damaged. This scar tissue also puts the patient at risk for potentially life threatening arrhythmias, and may result in the formation of a ventricular aneurysm that can rupture with catastrophic consequences. Injured heart tissue conducts electrical impulses more slowly than normal heart tissue. The difference in conduction velocity between injured and uninjured tissue can trigger re-entry or a feedback loop that is believed to be the cause of many lethal arrhythmias. Cardiac output and blood pressure may fall to dangerous levels, which can lead to further coronary ischemia and extension of the infarct.

In addition to the direct effects on the infarcted tissue, adjacent tissues in the borderzone around the infarct undergo a pathologic remodeling triggered by altered gene regulation. This remodeling results in further myocyte loss, hyperplasia and the further deposition of collagen in this region. Secondarily to the infarct, the remote myocardium responds to the infarct by cardiomyocyte hypertrophy and the onset of interstitial fibrosis. Thus, while the damage to the infarcted tissue maybe largely irreparable by the time an MI is diagnosed and addressed clinically, the further changes due to post-MI remodeling present a more likely point of therapeutic intervention. At present, however, there are no known treatments to address this aspect of heart disease.

Changes in gene expression and signaling pathways associated with post-MI remodeling have been intensively studied, with the goal of identifying therapeutic targets that might allow restoration of function to the injured heart. Recently, key roles of microRNAs in cardiac hypertrophy and heart failure have been described, pointing to a new mode of regulation of cardiac disease. MicroRNAs (miRNAs) are small, non-protein coding RNAs of about 18 to about 25 nucleotides in length that are derived from individual miRNA genes, from introns of protein coding genes, or from poly-cistronic transcripts that often encode multiple, closely related miRNAs. See review by Carrington et al. (*Science*, Vol. 301(5631):336-338, 2003). MiRNAs act as repressors of target mRNAs by promoting their degradation, when their sequences are perfectly complementary, or by inhibiting translation, when their sequences contain mismatches.

MiRNAs are transcribed by RNA polymerase II (pol II) or RNA polymerase III (pol III; see Qi et al. (2006) *Cellular & Molecular Immunology*, Vol. 3:411-419) and arise from initial transcripts, termed primary miRNA transcripts (pri-miRNAs), that are generally several thousand bases long. Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

Based on a hand full of genetic studies in mice and humans, it is becoming increasingly clear that miRNAs are indeed actively involved in cardiac remodeling, growth, conductance, and contractility (reviewed in van Rooij and Olson (2007) Journal of Clinical Investigation, Vol. 117(9):2369-2376). Identification and characterization of miRNAs involved in cardiovascular disease is important for the development of novel therapeutic approaches for the treatment of cardiovascular disease diseases, such as myocardial infarction and heart failure.

SUMMARY OF THE INVENTION

The present invention is based, in part, on the discovery of several miRNAs that are regulated in cardiac tissue following myocardial infarction and heart failure in humans. Modulation of these identified miRNAs presents a novel therapeutic approach for treating or preventing myocardial infarction, cardiac remodelling, and heart failure. Accordingly, the invention provides a method of treating or preventing myocardial infarction, cardiac remodelling, or heart failure in a subject in need thereof comprising modulating the expression or activity of one or more of the identified miRNAs in the heart cells of the subject. In one embodiment, the one or more miRNAs are selected from the group consisting of a let-7 family member, miR-15b, miR-21, miR-199a, miR-199b, miR-214, miR-10a, miR-10b, miR-16, miR-146a, miR-146b, miR-221, miR-222, miR-497, miR-20a, miR-20b, miR-93, miR-101, miR-126, a miR-30 family member, miR-143, miR-145, miR-150, miR-29a-c, miR-34a, miR-34c, miR-574, miR-451, miR-499, miR-100, miR-378, miR-24, miR-379, miR-762, miR-335, miR-711, miR-149, miR-218, miR-181a-d, miR-22, and miR-185.

In one embodiment, the method comprises administering to the subject an inhibitor of one or more of the identified miRNAs. For instance, the inhibitor can be an inhibitor of the expression or activity of a miRNA selected from the group consisting of a let-7 family member, miR-15b, miR-21, miR-199a, miR-199b, miR-214, miR-10a, miR-10b, miR-16, miR-146a, miR-146b, miR-221, miR-222, a miR-30 family member, and miR-497. The inhibitor of one or more miRNAs can include an antagomir, an antisense oligonucleotide, or an inhibitory RNA molecule.

In another embodiment, the method comprises administering to the subject an agonist of one or more of the identified miRNAs. In some embodiments, the agonist increases the expression or activity of a miRNA selected from the group consisting of miR-20a, miR-20b, miR-93, miR-101, miR-126, miR-143, miR-145, miR-150, miR-29a, miR-29b, and miR-29c. In certain embodiments, the agonist of one or more miRNAs is a polynucleotide comprising a mature sequence of the one or more miRNAs. The agonist can be expressed in vivo from an expression construct.

In some embodiments, the method may further comprising administering to the subject a second cardiac hypertrophic therapy, such as a β blocker, an ionotrope, a diuretic, ACE-I, AII antagonist, BNP, a $Ca^{++}$-blocker, an endothelin receptor antagonist, or an HDAC inhibitor. The second therapy may be administered at the same time as the miRNA modulator (e.g. inhibitor or agonist) or before or after the miRNA modulator.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. MiRNA profiling in response to MI. A. Masson Trichrome staining on cardiac sections indicates a scar formation 3 days after MI, with myocyte hypertrophy, ongoing loss of myocytes and the deposit of collagens. Fourteen days after infarct there is a thinned stretched infarct that results in cardiac hypertrophy and interstitial fibrosis in the non-infarcted region. (I, infarct; BZ, border-zone; R, remote myocardium). B. Microarray analysis indicates that miRNAs are very dynamically regulated in response to MI. Even after initial infarct healing, 14 days post-MI 11 miRs are overlappingly upregulated in the borderzone while 15 miRs are downregulated. C. Bargraph of up-regulated miRs (left panel) and down-regulated miRs (right panel) in the borderzone region both 3 days and 14 days post-MI. D. Real-time PCR analysis confirmed the regulation of miRNAs in response to MI compared to sham operated animals (n=3-4). E. Real-time PCR analysis for indicated miRNAs in human heart samples in response to MI compared to non-failing hearts (n=5-6). F. Northern blot analysis for miR-21 in 3 non-failing human hearts and 5 human hearts post-MI.

FIG. 2. MiR-29 is downregulated in the infarcted region after MI. A. Sequence alignment of miR-29 family members indicates a conserved seed region (bp 2-8 of the 5' end) and a high level of sequence conservation in the 3' end of the miRNA. B. Northern blot analysis of multiple tissues indicates a large overlap in expression for all three miR-29 members, with a high expression level in lungs and kidney. Of the miR-29 members, miR-29b appeared most highly expressed in the heart. C. Real-time PCR analysis for miR-29 indicated this miR to be highly expressed in fibroblasts compared to cardiomyocytes that were either kept in serum-free media (SF) or stimulated with phenylephrine (PE). D. Northern blot analysis of cardiac tissue 3 days post-MI shows a consistent downregulation of miR-29 in response to MI compared to sham operated animals. The downregulation of miR-29 is more pronounced in the borderzone than in the remote myocardium. E. Real-time PCR analysis indicates all miR-29 members to be regulated in response to MI. While the downregulation is most pronounced in the border zone (BZ) of the infarct 3 days after MI, this downregulation remains present 14 days after infarction when initial infarct healing has taken place.

FIG. 3. MiR-29 regulates the expression of extracellular matrix proteins. A. Potential binding sites for miR-29 in 3' UTR regions of key fibrotic genes. B. Real-time PCR analysis of predicted target genes in both the borderzone and remote myocardium 3 days after MI. A decrease in miR-29 expression correlates with an increase in expression of collagens (COL1A1, COL1A2 and COL3A1) and fibrillin (FBN1). No significant change in elastin (ELN1) was observed. C. Northern blot analysis on COS cells transfected with increasing amounts of the miR-29b-1/miR-29a cluster, shows efficient overexpression of miR-29. D. Luciferase experiments using the endogenous UTR sequences of the predicted target genes. Expression of miR-29b-1/miR-29a represses expression of luciferase, whereas repression was absent when an unrelated miR, miR-206, was expressed.

FIG. 4. MiR-29 expression is responsive to TGFβ. A. Real-time PCR analysis indicates that all three miR-29 family members are downregulated in fibroblasts in response to TGFβ. B. Northern analysis showing miR-29 expression is upregulated in miR-208 mutant animals which coincides with an increase in BNP expression as determined by real-time PCR.

FIG. 5. MiR-29 inhibition induces fibrosis in vivo. A. Chemical structure of anti-miR-29 and mismatch (mm) miR-29 oligonucleotides. B. Northern blot analysis showing tissue specific knockdown after 3 days in response to intravenous injection of 80 mg/kg of either anti-miR-29 or mm miR-29 or a comparable volume of saline. C. Real-time PCR analysis of liver extracts indicate a pronounced increase in collagen expression in response to miR-29 knockdown. This effect was absent after saline or mm miR-29 injection. D. Northern blot analysis of tissue collected three weeks after intravenous injection with 80 mg/kg on two consecutive days of either anti-miR-29 or mm miR-29 oligonucleotide or a comparable volume of saline. Injection of anti-miR-29 produced a severe knockdown of miR-29 in heart, liver and kidney, while miR-29 levels in lungs appeared unaffected. E. Real-time PCR analysis of heart extracts indicate a increase in cardiac collagen expression in response to miR-29 knockdown. F. Real-time PCR analysis indicating an increase in miR-29b expression in fibroblasts two days after miR-29b mimic treatment, while miR-29a levels were unchanged and miR-29c levels only slightly increased. G. MiR-29b overexpression in fibroblasts represses the expression of collagen genes as determined by real-time PCR analysis.

DETAILED DESCRIPTION OF THE INVENTION

The present invention is based, in part, on the identification of a subset of miRNAs that are regulated following myocardial infarction. In particular, the inventors discovered 40 miRNAs that were significantly regulated in the border zone of the infarcted region and 22 miRNAs that were regulated in the remote myocardium three days after induction of myocardial infarction (MI). Furthermore, expression of 69 miRNAs was changed in the border zone of the infarcted region two weeks after induction of MI, while 40 miRNAs were regulated in the remote myocardium. In addition, the inventors discovered a different, but overlapping subset of miRNAs to be regulated in cardiac tissue from failing human hearts. Thirty one miRNAs were found to be significantly upregulated, while 45 miRNAs were significantly downregulated in the cardiac tissue from human heart failure patients. The overlap in regulated miRNAs suggests that these miRNAs may be involved in different cardiac disease processes and actively influence the disease state. Accordingly, the present invention provides a method of treating or preventing myocardial infarction, cardiac remodelling, or heart failure in a subject in need thereof comprising modulating the expression or activity of one or more miRNAs listed in Tables 3-6 in the heart cells of the subject. In certain embodiments, the one or more miRNAs is selected from the group consisting of a let-7 family member (e.g. let-7a, let-7b, let-7c, let-7d, let-7e, let-7f, let-7g, and let-7l) (SEQ ID NOs: 1-8), miR-15b (SEQ ID NO: 9), miR-21 (SEQ ID NO: 10), miR-199a (SEQ ID NO: 11), miR-199b (SEQ ID NOs: 12-13), miR-214 (SEQ ID NO: 14), miR-10a (SEQ ID NO: 15), miR-10b (SEQ ID NO: 16), miR-16 (SEQ ID NO: 17), miR-146a (SEQ ID NO: 18), miR-146b (SEQ ID NOs: 19-20), miR-221 (SEQ ID NO: 21), miR-222 (SEQ ID NO: 22), miR-497 (SEQ ID NO: 23), miR-20a (SEQ ID NO: 24), miR-20b (SEQ ID NO: 25), miR-93 (SEQ ID NO: 26), miR-101 (SEQ ID NO: 27), miR-126 (SEQ ID NO: 28), a miR-30 family member (e.g. miR-30a, miR-30b, miR-30c, miR-30d, and miR-30e) (SEQ ID NOs: 29-33), miR-143 (SEQ ID NO: 34), miR-145 (SEQ ID NO: 35), miR-150 (SEQ ID NO: 36), miR-29a-c (SEQ ID NOs: 37-39), miR-34a (SEQ ID NO: 40), miR-34c (SEQ ID NOs: 41-42), miR-574 (SEQ ID NOs: 43-44), miR-451 (SEQ ID NO: 45), miR-499 (SEQ ID NO: 46), miR-100 (SEQ ID NO: 47), miR-378 (SEQ ID NO: 48), miR-24 (SEQ ID NO: 49), miR-379 (SEQ ID NO: 50), miR-762 (SEQ ID NO: 51), miR-335 (SEQ ID NO: 52), miR-711 (SEQ ID NO: 53), miR-149 (SEQ ID NO: 54), miR-218 (SEQ ID NO: 55), miR-181a-d (SEQ ID NOs: 56-59), miR-22 (SEQ ID NO: 60), and miR-185 (SEQ ID NO: 61).

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some embodiments, the subject is a mammal. In other embodiments, the subject is a human. In such embodiments in which the subject to be treated is human, the one or more miRNAs to be modulated are human miRNA sequences.

As used herein, the term "modulate" refers to a change or an alteration in a biological activity of a miRNA. Modulation may be a change in the expression level of the miRNA, a change in binding characteristics of the miRNA (e.g. to a target mRNA or to a component of the RISC complex), or any other change in the biological or functional properties associated with the miRNA. Modulation can be either an increase or decrease in the expression or function of the miRNA. The term "modulator" refers to any molecule or compound which is capable of changing or altering the expression or biological activity of a miRNA as described above.

In one embodiment, the method comprises administering an inhibitor of one or more miRNAs (or corresponding human miRNAs) listed in Tables 3-6 to the subject. In some embodiments, the inhibitor targets the pre-miRNA or pri-miRNA sequences. In other embodiments, the inhibitor targets the mature miRNA sequence. In another embodiment, the inhibitor is an inhibitor of the expression or activity of one or more mature miRNA sequences selected from the group consisting of a let-7 family member (e.g. let-7a, let-7b, let-7c, let-7d, let-7e, let-7f, let-7g, and let-7l) (SEQ ID NOs: 1-8), miR-15b (SEQ ID NO: 9), miR-21 (SEQ ID NO: 10), miR-199a (SEQ ID NO: 11), miR-199b (SEQ ID NOs: 12-13), miR-214 (SEQ ID NO: 14), miR-10a (SEQ ID NO: 15), miR-10b (SEQ ID NO: 16), miR-16 (SEQ ID NO: 17), miR-146a (SEQ ID NO: 18), miR-146b (SEQ ID NOs: 19-20), miR-221 (SEQ ID NO: 21), miR-222 (SEQ ID NO: 22), miR-497 (SEQ ID NO: 23), and a miR-30 family member (e.g. miR-30a, miR-30b, miR-30c, miR-30d, and miR-30e) (SEQ ID NOs: 29-33).

In certain embodiments, the inhibitor of one or more miRNAs is an antisense oligonucleotide. The antisense oligonucleotides can include ribonucleotides or deoxyribonucleotides or a combination thereof. Preferably, the antisense oligonucleotides have at least one chemical modification (e.g., sugar or backbone modification). For instance, suitable antisense oligonucleotides may be comprised of one or more "conformationally constrained" or bicyclic sugar nucleoside modifications (BSN) that confer enhanced thermal stability to complexes formed between the oligonucleotide containing BSN and their complementary microRNA target strand. For example, in one embodiment, the antisense oligonucleotides contain at least one "locked nucleic acid." Locked nucleic acids (LNAs) contain the 2'-O, 4'-C-methylene ribonucleoside (structure A) wherein the ribose sugar moiety is in a "locked" conformation. In another embodiment, the antisense oligonucleotides contain at least one 2',4'-C-bridged 2' deoxyribonucleoside (CDNA, structure B). See, e.g., U.S. Pat. No. 6,403,566 and Wang et al. (1999) Bioorganic and Medicinal Chemistry Letters, Vol. 9: 1147-1150, both of which are herein incorporated by reference in their entireties. In yet another embodiment, the antisense oligonucleotides contain at least one modified nucleoside having the structure shown in structure C. The antisense oligonucleotides targeting one or more miRNAs can contain combinations of BSN (LNA, CDNA and the like) or other modified nucleotides, and ribonucleotides or deoxyribonucleotides.

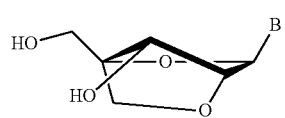

A

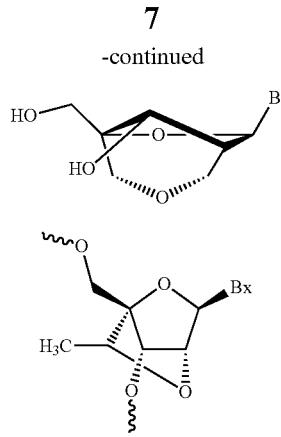

Alternatively, the antisense oligonucleotides can comprise peptide nucleic acids (PNAs), which contain a peptide-based backbone rather than a sugar-phosphate backbone. Other modified sugar or phosphodiester modifications to the antisense oligonucleotide are also contemplated. For instance, other chemical modifications that the antisense oligonucleotides can contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In one embodiment, antisense oligonucleotides targeting one or more miRNAs contain 2'O-methyl sugar modifications on each base and are linked by phosphorothioate linkages. Antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O-alkyl modifications and the like. In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. For instance, to facilitate in vivo delivery and stability, the antisense oligonucleotide may be linked to a steroid, such as cholesterol moiety, a vitamin, a fatty acid, a carbohydrate or glycoside, a peptide, or other small molecule ligand at its 3' end.

Preferable antisense oligonucleotides useful for inhibiting the activity of miRNAs are about 5 to about 25 nucleotides in length, about 10 to about 30 nucleotides in length, or about 20 to about 25 nucleotides in length. In certain embodiments, antisense oligonucleotides targeting one or more of the miRNAs described herein are about 8 to about 18 nucleotides in length, and in other embodiments about 12 to about 16 nucleotides in length. Any 8-mer or longer complementary to the target miRNA may be used, i.e., any antimiR complementary to the 5' end of the miRNA and progressing across the full complementary sequence of the target miRNA. Antisense oligonucleotides can comprise a sequence that is at least partially complementary to a mature miRNA sequence from one or more miRNAs. "Partially complementary" refers to a sequence that is at least about 75%, 80%, 85%, 90%, 95%, 96%, 97%, 98%, or 99% complementary to a target miRNA sequence. In some embodiments, the antisense oligonucleotide can be substantially complementary to a mature miRNA sequence, that is at least about 90%, 95%, 96%, 97%, 98%, or 99% complementary to a target miRNA sequence. In one embodiment, the antisense oligonucleotide comprises a sequence that is 100% complementary to a mature miRNA sequence.

In some embodiments, the antisense oligonucleotides are antagomirs. "Antagomirs" are single-stranded, chemically-modified ribonucleotides that are at least partially complementary to at least one mature miRNA sequence. Antagomirs may comprise one or more modified nucleotides, such as 2'-O-methyl-sugar modifications. In some embodiments, antagomirs comprise only modified nucleotides. Antagomirs can also comprise one or more phosphorothioate linkages resulting in a partial or full phosphorothioate backbone. To facilitate in vivo delivery and stability, the antagomir can be linked to a cholesterol or other moiety at its 3' end. Antagomirs suitable for inhibiting one or more miRNA family members can be about 15 to about 50 nucleotides in length, more preferably about 18 to about 30 nucleotides in length, and most preferably about 20 to about 25 nucleotides in length. The antagomirs can be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 90%, 95%, 96%, 97%, 98%, or 99% complementary to a target polynucleotide sequence. In other embodiments, the antagomirs are 100% complementary to a mature miRNA sequence.

In another embodiment, the method comprises administering an agonist of one or more miRNAs (or corresponding human miRNAs) listed in Tables 3-6 to the subject. In certain embodiments, the agonist is an agonist of one or more miRNAs selected from the group consisting of miR-20a (SEQ ID NO: 24), miR-20b (SEQ ID NO: 25), miR-93 (SEQ ID NO: 26), miR-101 (SEQ ID NO: 27), miR-126 (SEQ ID NO: 28), miR-143 (SEQ ID NO: 34), miR-145 (SEQ ID NO: 35), miR-150 (SEQ ID NO: 36), miR-29a (SEQ ID NO: 37), miR-29b (SEQ ID NO: 38), and miR-29c (SEQ ID NO: 39).

As used herein, an "agonist" is a molecule or compound that enhances the expression or activity of a target miRNA. An agonist can be a polynucleotide encoding the miRNA sequence. For instance, in one embodiment, an agonist of one or more miRNAs is a polynucleotide comprising a mature sequence of the one or more miRNAs. In another embodiment, the agonist of one or more miRNAs can be a polynucleotide comprising the pri-miRNA or pre-miRNA sequence for the one or more miRNAs. The polynucleotide comprising the mature, pre-miRNA, or pri-miRNA sequence can be single stranded or double stranded. The polynucleotides may contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In some embodiments, the polynucleotide comprising one or more miRNA sequences is conjugated to a steroid, such as cholesterol, a vitamin, a fatty acid, a carbohydrate or glycoside, a peptide, or another small molecule ligand. In certain embodiments, an agonist of one or more miRNAs is an agent distinct from the miRNA itself that acts to increase, supplement, or replace the function of the one or more miRNAs.

The inhibitors and agonists of the miRNAs of the invention can be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing an agonist of one or more miRNAs comprises a promoter "operably linked" to a polynucleotide encoding a sequence of the one or more miRNAs. The phrase "operably linked" or "under transcriptional control" as used herein means that the promoter is in the correct location and orientation in relation to a polynucleotide to control the initiation of transcription by RNA polymerase and expression of the polynucleotide. The polynucleotide encoding one or more miRNAs may encode the primary microRNA sequence, the precursor-microRNA sequence, the mature miRNA sequence, or the star (e.g. minor) sequence of the one or more miRNAs described herein. The polynucleotide comprising a sequence of one or more miRNAs can be about 18 to about 2000 nucleotides in length, about 70 to about 200 nucleotides in length, about 20 to about 50 nucleotides in length, or about 18 to about 25 nucleotides in length.

Inhibitors of one or more miRNAs (e.g., antisense oligonucleotides and antagomirs) can be expressed from a vector in vivo. For instance, in one embodiment, an expression vector for expressing an inhibitor of one or more miRNAs comprises a promoter operably linked to a polynucleotide encoding an antisense oligonucleotide, wherein the sequence of the expressed antisense oligonucleotide is at least partially complementary to the mature sequence of one or more miRNAs.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III.

In some embodiments, the human cytomegalovirus (CMV) immediate early gene promoter, the SV40 early promoter, the Rous sarcoma virus long terminal repeat, rat insulin promoter, and glyceraldehyde-3-phosphate dehydrogenase promoter can be used to obtain high-level expression of the polynucleotide sequence of interest. The use of other viral or mammalian cellular or bacterial phage promoters, which are well-known in the art to achieve expression of a polynucleotide sequence of interest, is contemplated as well, provided that the levels of expression are sufficient for a given purpose.

By employing a promoter with well-known properties, the level and pattern of expression of the polynucleotide of interest following transfection or transformation can be optimized. Further, selection of a promoter that is regulated in response to specific physiologic signals can permit inducible expression of the polynucleotide. Tables 1 and 2 list several regulatory elements that may be employed, in the context of the present invention, to regulate the expression of the polynucleotide of interest (e.g. agonists or inhibitors of miRNAs of the invention). This list is not intended to be exhaustive of all the possible elements involved in the promotion of gene expression but, merely, to be exemplary thereof.

Below is a list of viral promoters, cellular promoters/enhancers and inducible promoters/enhancers that could be used in combination with the polynucleotide of interest in an expression construct (Table 1 and Table 2). Additionally, any promoter/enhancer combination (as per the Eukaryotic Promoter Data Base EPDB) could also be used to drive expression of the polynucleotide. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/ or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |

TABLE 1-continued

Promoter and/or Enhancer

| Promoter/Enhancer | References |
|---|---|
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

A polyadenylation signal may be included to effect proper polyadenylation of the gene transcript where desired. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with or as an indicator of the nucleic acid encoding a gene product. Further examples of selectable markers are well known to one of skill in the art.

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Other viral vectors may be employed as expression constructs in the present invention. Vectors derived from viruses such as retrovirus, vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a polynucleotide of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular polynucleotide of interest may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In a particular example, the polynucleotide may be administered in combination with a cationic lipid or neutral lipid, or a combination of cationic and anionic lipids that together result in a neutral charge (see e.g. WO05007196 and WO05026372, which are herein incorporated by reference in their entireties). Examples of cationic lipids include, but are not limited to, lipofectin, DOTMA, DOPE, and DOTAP. The publication of WO0071096, which is specifically incorporated by reference, describes different formulations, such as a DOTAP:cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Preferably, administration of an inhibitor or agonist of one or more miRNAs (or corresponding human miRNAs) listed in Tables 3-6 results in the improvement of one or more symptoms of myocardial infarction, heart failure, or cardiac remodeling. The one or more improved symptoms can be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, decreased wall tension, increased quality of life, and decreased disease related morbidity or mortality. In one embodiment, modulation of one or more miRNAs in the heart cells of a subject suffering from myocardial infarction can reduce infarct size by decreasing the loss of heart cells (e.g. decreasing apoptosis in the infarct zone). In another embodiment, modulation of one or more miRNAs in the heart cells of a subject suffering from myocardial infarction can reduce fibrosis in the infarct zone. In still another embodiment, cardiac function is stabilized in a subject suffering from myocardial infarction following modulation of one or more miRNAs in the heart cells of the subject.

The present invention contemplates the use of agonists and inhibitors of identified miRNAs in the treatment and prevention of post-MI remodeling of cardiac tissues that surround an infarct as well as the subsequent development of heart failure in a subject. Treatment regimens would vary depending on the clinical situation, with earliest intervention being sought. However, long-term maintenance for at least some period of time post-MI would appear to be appropriate in most circumstances. It also may be desirable to treat with modulators of miRNAs intermittently, or to vary which miRNAs are given, in order to maximize the protective effects.

In another embodiment, it is envisioned to use a modulator of miRNA function or expression in combination with other therapeutic modalities. Thus, in addition to the miRNA therapies described above, one may also provide to the subject more "standard" pharmaceutical cardiac therapies. Examples of other therapies include, without limitation, so-called "β-blockers," anti-hypertensives, cardiotonics, anti-thrombotics, vasodilators, hormone antagonists, iontropes, diuretics, endothelin receptor antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or a pharmacological formulation that includes one or more miRNA modulators and a second cardiac therapy, or by contacting the cell with two distinct compositions or formulations, at the same time, wherein one composition includes one or more miRNA modulators and the other includes the second cardiac therapy. Alternatively, administration of one or miRNA modulators may precede or follow administration of the other cardiac agent(s) by intervals ranging from minutes to weeks. In embodiments where the other cardiac agent and one or miRNA modulators are applied separately to the subject, one would generally ensure that a significant period of time did not expire between the time of each delivery, such that the cardiac agent and one or miRNA modulators would still be able to exert an advantageously combined effect on the cell. In such instances, it is contemplated that one would typically administer the two compositions within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a modulator of one or more miRNAs, or the other cardiac agent will be desired. In this regard, various combinations may be employed. By way of illustration, where the miRNA modulator is "A" and the other cardiac agent is "B," the following permutations based on 3 and 4 total administrations are exemplary:

```
A/B/A  B/A/B  B/B/A  A/A/B  B/A/A  A/B/B  B/B/B/A

B/B/A/B  A/A/B/B  A/B/A/B  A/B/B/A  B/B/A/A  B/A/B/A

B/A/A/B  B/B/B/A  A/A/A/B  B/A/A/A  A/B/A/A  A/A/B/A

A/B/B/B  B/A/B/B  B/B/A/B
```

Other combinations are likewise contemplated.

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in combination with the miRNA modulators of the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In certain embodiments, administration of an agent that lowers the concentration of one of more blood lipids and/or lipoproteins, known herein as an "antihyperlipoproteinemic," may be combined with a cardiovascular therapy according to the present invention (e.g. miRNA modulator), particularly in treatment of atherosclerosis and thickenings or blockages of vascular tissues. In certain embodiments, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof. Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate. Non-limiting examples of resins/bile acid sequesterants include cholestyramine (cholybar, questran), colestipol (colestid) and polidexide. Non-limiting examples of HMG CoA reductase inhibitors include lovastatin (mevacor), pravastatin (pravochol) or simvastatin (zocor). Non-limiting examples of nicotinic acid derivatives include nicotinate, acepimox, niceritrol, nicoclonate, nicomol and oxiniacic acid. Non-limiting examples of thyroid hormones and analogs thereof include etoroxate, thyropropic acid and thyroxine.

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin. A non-limiting example of an antiarteriosclerotic includes pyridinol carbamate.

In certain embodiments, administration of an agent that aids in the removal or prevention of blood clots may be combined with administration of a miRNA modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof. In certain embodiments, antithrombotic agents that can be administered orally, such as, for example, aspirin and wafarin (coumadin), are preferred.

In some embodiments, the miRNA modulator can be combined with one or more anticoagulants. Non-limiting examples of anticoagulants include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

The miRNA modulator can be combined with an antiplatelet agent and/or a thrombolytic agent. Non-limiting examples of antiplatelet agents include aspirin, a dextran, dipyridamole (persantin), heparin, sulfinpyranone (anturane) and ticlopidine (ticlid). Non-limiting examples of thrombolytic agents include tissue plaminogen activator (activase), plasmin, pro-urokinase, urokinase (abbokinase) streptokinase (streptase), anistreplase/APSAC (eminase).

In certain embodiments wherein a patient is suffering from a hemorrhage or an increased likelihood of hemorrhaging, an agent that may enhance blood coagulation may be used in combination with a miRNA modulator. Non-limiting examples of blood coagulation promoting agents include thrombolytic agent antagonists and anticoagulant antagonists. Non-limiting examples of anticoagulant antagonists include protamine and vitamin K1.

Non-limiting examples of thrombolytic agent antagonists that can be combined with a miRNA modulator include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

In certain embodiments, a miRNA modulator can be combined with an antiarrhythmic agent for the treatment of cardiovascular conditions. Non-limiting examples of antiarrhythmic agents include Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythmic agents.

Sodium channel blockers include, but are not limited to, Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor).

Exemplary beta blockers, otherwise known as a β-adrenergic blockers, β-adrenergic antagonists or Class II antiarrhythmic agents, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain embodiments, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

Examples of Class III antiarrhythmic agents include agents that prolong repolarization, such as amiodarone (cordarone) and sotalol (β-pace). Non-limiting examples of Class IV antiarrythmic agents, also known as calcium channel blockers, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

Suitable examples of miscellaneous antiarrhythmic agents that can also be combined with a miRNA modulator of the invention include, but are not limited to, adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

In yet another embodiment of the invention, the miRNA modulator can be administered in combination with an antihypertensive agent. Non-limiting examples of antihypertensive agents include sympatholytic, alpha/beta blockers, alpha blockers, anti-angiotensin II agents, beta blockers, calcium channel blockers, vasodilators and miscellaneous antihypertensives.

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an alpha and beta adrenergic antagonist. Non-limiting examples of an alpha/beta blocker comprise labetalol (normodyne, trandate).

Non-limiting examples of anti-angiotensin II agents include angiotensin converting enzyme inhibitors and angiotensin II receptor antagonists. Non-limiting examples of angiotensin converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotensin II receptor antagonist, an ANG receptor blocker or an ANG-II type-1 receptor blocker (ARBS), include angiocandesartan, eprosartan, irbesartan, losartan and valsartan.

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting examples of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (naimodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

In certain embodiments a cardiovasculator therapeutic agent may comprise a vasodilator (e.g., a cerebral vasodilator, a coronary vasodilator or a peripheral vasodilator) that can be co-administered with a miRNA modulator of the invention. In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine.

In certain embodiments, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive may comprise an aryletanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlomethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril. Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide.

In another embodiment, a miRNA modulator of the invention can be co-administered with a vasopressor. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

In certain embodiments, a miRNA modulator of the invention can be administered in combination with a treatment for congestive heart failure. Exemplary agents for the treatment of congestive heart failure include, but are not limited to, anti-angiotensin II agents, afterload-preload reduction treatment, diuretics and inotropic agents. Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

In certain embodiments, an animal patient that can not tolerate an angiotensin antagonist may be treated with a combination therapy, such as administration of hydralazine (apresoline) and isosorbide dinitrate (isordil, sorbitrate) with a miRNA modulator.

A miRNA modulator of the invention can be combined with an inotropic agent. In some embodiments, the inotropic agent is a positive inotropic agent. Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular embodiments, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor).

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

In certain embodiments, a miRNA modulator of the invention is co-administered with endothelin for treatment of a cardiovascular disease. Endothelin (ET) is a 21-amino acid peptide that has potent physiologic and pathophysiologic effects that appear to be involved in the development of heart failure. The effects of ET are mediated through interaction with two classes of cell surface receptors. The type A receptor (ET-A) is associated with vasoconstriction and cell growth while the type B receptor (ET-B) is associated with endothelial-cell mediated vasodilation and with the release of other neurohormones, such as aldosterone. Pharmacologic agents that can inhibit either the production of ET or its ability to stimulate relevant cells are known in the art. Inhibiting the production of ET involves the use of agents that block an enzyme termed endothelin-converting enzyme that is involved in the processing of the active peptide from its precursor. Inhibiting the ability of ET to stimulate cells involves the use of agents that block the interaction of ET with its receptors. Non-limiting examples of endothelin receptor antagonists (ERA) include Bosentan, Enrasentan, Ambrisentan, Darusentan, Tezosentan, Atrasentan, Avosentan, Clazosentan, Edonentan, sitaxsentan, TBC 3711, BQ 123, and BQ 788.

In certain embodiments, the secondary therapeutic agent that can be combined with the miRNA modulator may comprise a surgery of some type, which includes, for example, preventative, diagnostic or staging, curative and palliative surgery. Surgery, and in particular a curative surgery, may be used in conjunction with other therapies, such as the miRNA modulators of the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

Where clinical applications are contemplated, pharmaceutical compositions comprising a modulator of one or miRNAs identified in Tables 3-6 will be prepared in a form appropriate for the intended application. Generally, this will entail preparing compositions that are essentially free of pyrogens, as well as other impurities that could be harmful to humans or animals. Colloidal dispersion systems, such as macromolecule complexes, nanocapsules, microspheres, beads, and lipid-based systems including oil-in-water emulsions, micelles, mixed micelles, and liposomes, may be used as delivery vehicles for the oligonucleotide inhibitors of microRNA function or miRNA agonists (e.g. constructs expressing particular miRNAs or polynucleotides encoding miRNAs). Commercially available fat emulsions that are suitable for delivering the nucleic acids of the invention to tissues, such as cardiac muscle tissue, include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are herein incorporated by reference in their entireties.

One will generally desire to employ appropriate salts and buffers to render nucleic acids, agonists, inhibitors, and delivery vectors stable and allow for uptake by target cells. Buffers also will be employed when recombinant cells are introduced into a patient. Aqueous compositions of the present invention comprise an effective amount of the agent, dissolved or dispersed in a pharmaceutically acceptable carrier or aqueous medium. The phrases "pharmaceutically acceptable" or "pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or nucleic acids of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Pharmaceutical compositions comprising miRNA inhibitors or agonists may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e., the ability of the heart to pump blood).

"Improvement in the physiologic function" of the heart may be assessed using any of the measurements described herein (e.g., measurement of ejection fraction, fractional shortening, left ventricular internal dimension, heart rate, etc.), as well as any effect upon the animal's survival.

As used herein, the term "cardiac hypertrophy" refers to the process in which adult cardiac myocytes respond to stress through hypertrophic growth. Such growth is characterized by cell size increases without cell division, assembling of additional sarcomeres within the cell to maximize force generation, and an activation of a fetal cardiac gene program. Cardiac hypertrophy is often associated with increased risk of morbidity and mortality, and thus studies aimed at understanding the molecular mechanisms of cardiac hypertrophy could have a significant impact on human health.

The term "myocardial infarction," or MI, is the rapid development of myocardial necrosis caused by an imbalance between oxygen supply and demand of the myocardium, often resulting from plaque rupture with thrombus formation in a coronary vessel, resulting in an acute reduction of blood supply to a portion of the myocardium. Many MI events are either "silent" or are clinically unrecognized, but are nonetheless encompassed within this definition. The appearance of cardiac markers in the circulation generally indicates myocardial necrosis and is a useful adjunct to diagnosis. Such markers included ST-elevation MI (STEMI), non-ST-elevation MI (NSTEMI), and unstable angina.

It is contemplated that any embodiment discussed herein can be implemented with respect to any method or composition of the invention, and vice versa. Furthermore, compositions and kits of the invention can be used to achieve methods of the invention. Throughout this application, the term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

Identification of MicroRNAs Regulated During Post-Myocardial Infarction Remodeling During post-myocardial infarction (post-MI) remodeling, the left ventricle can roughly be divided into two regions: (a) the infarcted region and (b) the remote myocardium. Extensive fibrosis and myocyte loss are major features of the initial phase of myocardial remodeling during infarct healing, while cardiomyocyte hypertrophy and interstitial fibrosis occur in the non-infarcted myocardium post-MI (FIG. 1A). In an effort to identify miRNAs involved in post-MI remodeling, MI was induced by occlusion of the left anterior descending artery (LAD) and miRNA expression profiles were compared in mouse hearts 3 and 14 days after MI in both the borderzone of the infarcted region and the non-infarcted (remote) myocardium to the miRNA expression profile of sham-operated animals (FIG. 1B-C and Tables 3 and 4). Among 569 individual miRNAs represented on the microarrays, 40 miRNAs were significantly regulated in the border zone of the infarcted region three days after induction of MI; 17 miRNAs showed a 2-fold or greater increase in expression and 23 miRNAs showed a 2-fold or greater decrease in expression. In addition, 22 miRNAs appeared to be changed in the remote myocardium; 12 miRNAs showed a 2-fold or greater increase in expression and 10 miRNAs showed a 2-fold or greater decrease in expression (Tables 3 and 4). Two weeks after MI, 69 miRNAs were regulated more than 2-fold in the border zone of the infarcted region, while 40 miRNAs showed a greater than 2-fold change in the remote myocardium (Tables 3 and 4). The array data were confirmed by real-time PCR analysis using miRNA-specific probes (FIG. 1D).

TABLE 3

Significantly upregulated miRNAs in response to MI (>2 fold change)

| miR | Border zone of infarcted area (fold change) | | Remote myocardium (fold change) | |
|---|---|---|---|---|
| | 3 days | 14 days | 3 days | 14 days |
| miR-21 | 6.3 | 14.8 | 2.6 | 12.6 |
| miR-15b | 3.9 | 3.5 | | 3.4 |
| miR-223 | 15.5 | 3.2 | | 6.0 |
| miR-214 | 6.5 | 6.9 | 2.4 | |
| miR-132 | 3.2 | | | |
| miR-222 | 2.8 | | 2.6 | |
| miR-483 | 6.3 | | | |
| miR-199a-3p | 2.1 | 3.6 | | |
| miR-379 | 3.3 | 12.0 | | |
| miR-221 | 2.0 | | | |
| miR-762 | 12.6 | 19.3 | 2.5 | |
| miR-92b | 2.3 | | | |
| miR-146b | 3.5 | 14.8 | | 6.6 |
| miR-705 | 2.5 | 6.2 | | |
| miR-574-5p | 39.7 | 54.9 | | |
| miR-335-5p | 2.4 | 17.4 | | 12.0 |
| miR-711 | 19.2 | | | |
| miR-218 | | 2.1 | | 2.2 |
| miR-739 | | 12.0 | | 5.4 |
| let-7e | | 41.4 | | 3.1 |
| miR-10b | | 11.2 | | 10.8 |
| miR-923 | | 19.8 | | 5.9 |
| let-7j | | 39.9 | | 37.8 |
| miR-199* | | 4.3 | | |
| let-7g | | 23.6 | | 21.7 |
| miR-16 | | 9.8 | | 9.8 |
| miR-638 | | 12.2 | | 3.0 |
| miR-10a | | 8.4 | | 10.3 |
| miR-146a | | 2.4 | | |
| let-7h | | 15.3 | | 10.0 |
| miR-26b | | 2.2 | | 2.1 |
| miR-155 | | 9.5 | | 2.2 |
| miR-352 | | 2.7 | | 2.3 |
| let-7d | | 2.2 | | |
| let-7b | | 23.1 | | 15.7 |
| miR-365 | | | | 12.6 |
| miR-34a | | | 2.0 | |
| miR-107 | | | 2.0 | |
| miR-103 | | | 2.1 | |
| miR-140* | | | 4.2 | 2.7 |
| miR-127 | | | | 2.9 |
| miR-497 | | | | 4.7 |

TABLE 3-continued

Significantly upregulated miRNAs in response to MI (>2 fold change)

| miR | Border zone of infarcted area (fold change) | | Remote myocardium (fold change) | |
|---|---|---|---|---|
| | 3 days | 14 days | 3 days | 14 days |
| miR-199a-5p | | 10.3 | | 2.8 |
| miR-199b* | | 196.9 | | 2.1 |

TABLE 4

Significantly downregulated miRNAs in response to MI (>2 fold change)

| miR | Border zone of infarcted area (fold change) | | Remote myocardium (fold change) | |
|---|---|---|---|---|
| | 3 days | 14 days | 3 days | 14 days |
| miR-149 | 11.5 | | | |
| miR-101b | 7.6 | 20.1 | | |
| miR-133a* | 7.0 | 4.8 | | |
| miR-101a | 7.9 | | | 4.3 |
| miR-24-2* | 3.7 | 2.6 | | |
| miR-218 | 4.8 | | 2.1 | |
| miR-126-5p | 64.4 | | 67.6 | |
| miR-145* | 3.6 | 4.8 | | |
| miR-689 | 2.1 | | | |
| miR-22 | 3.0 | 5.3 | | 3.6 |
| miR-499 | 2.1 | 4.2 | | |
| miR-30a* | 3.2 | 2.1 | 2.0 | |
| miR-22* | 2.7 | 5.0 | | 2.3 |
| miR-192 | 2.7 | | | |
| miR-194 | 3.6 | 7.0 | | 2.8 |
| miR-29c | 3.6 | 3.1 | | |
| miR-30e | 3.8 | 4.7 | | 3.0 |
| miR-130a | 2.3 | 2.7 | | |
| miR-181d | 3.8 | | 3.2 | 2.6 |
| miR-100 | 2.5 | | | |
| miR-29b | 11.4 | 2.2 | 2.0 | |
| miR-30e* | 4.0 | 3.0 | 2.3 | |
| miR-29a | 4.2 | 13.0 | 2.0 | |
| miR-690 | | 3.9 | | 2.4 |
| miR-106a | | 3.1 | | |
| miR-17-5p | | 3.8 | | 2.3 |
| miR-451 | | 2.8 | | |
| miR-143 | | 4.0 | | 2.0 |
| miR-34c-3p | | 89.9 | | 7.7 |
| miR-93 | | 3.9 | | 3.1 |
| miR-30a | | 2.5 | | |
| miR-148a | | 2.1 | | |
| miR-34a | | 4.4 | | 6.4 |
| miR-106b | | 4.3 | | 2.3 |
| miR-22b | | 4.1 | | 2.8 |
| miR-378 | | 3.9 | | 2.7 |
| miR-150 | | 2.9 | | |
| miR-128a | | 3.2 | | |
| miR-185 | | 4.0 | | 3.8 |
| miR-139 | | 2.3 | | |
| miR-423-5p | | 2.2 | | 3.0 |
| miR-320 | | 2.0 | | 3.4 |
| miR-20a | | 3.1 | | |
| miR-20b | | 2.8 | | |
| miR-103 | | 2.3 | | 2.2 |
| miR-352 | | | 2.2 | |
| miR-155 | | | 2.4 | |
| miR-218 | | | 2.1 | |

To examine the regulation of these identified miRNAs in human hearts, cardiac tissue from the borderzone of the infarcted region from patients receiving cardiac transplant was obtained. Real-time PCR analysis confirmed that several of the regulated miRNAs in the murine MI model were regulated similarly in human hearts. For instance, miR-21, miR-214 and miR-223 showed a striking increase in expression in the border zone of the infarct, while the expression of miR-29b and miR-149 was significantly downregulated (FIG. 1E). Northern blot analysis for miR-21 verified the real-time expression data (FIG. 1F). These results reveal a collection of miRNAs that are regulated during cardiac remodeling in response to ischemia.

Specific Methods

Surgical Procedures.

Adult C57/BL6 male mice were anesthetized with 2.4% isoflurane and placed in a supine position on a heating pad (37° C.). Animals were intubated with a 19G stump needle and ventilated with room air using a MiniVent mouse ventilator (Hugo Sachs Elektronik, Germany; stroke volume 250 µl, respiratory rate 210 breaths per minute). Via left thoracotomy between the fourth and fifth ribs, the left anterior descending artery (LAD) was visualized under a microscope and ligated using a 6-0 prolene suture. Regional ischemia was confirmed by visual inspection under a dissecting microscope (Leica) by discoloration of the occluded distal myocardium. Sham operated animals underwent the same procedure without occlusion of the LAD artery.

Histological Analysis and RNA In Situ Hybridization.

Tissues used for histology were incubated in Krebs-Henselheit solution, fixed in 4% paraformaldehyde, sectioned, and processed for hematoxylin and eosin (H&E) and Masson's Trichrome staining or in situ hybridization by standard techniques (Shelton et al., 2000).

Microarray for miRNAs. Microarray assay was performed using a service provider (LC Sciences). The assay started from 10 µg total RNA sample, which was size fractionated using a YM-100 Microcon centrifugal filter (from Millipore) and the small RNAs (<300 nt) isolated were 3'-extended with a poly(A) tail using poly(A) polymerase. An oligonucleotide tag was then ligated to the poly(A) tail for later fluorescent dye staining; two different tags were used for the two RNA samples in dual-sample experiments. Hybridization was performed overnight on a µParaflo microfluidic chip using a micro-circulation pump (Atactic Technologies) (Gao et al., 2004). On the microfluidic chip, each detection probe consisted of a chemically modified nucleotide coding segment complementary to target microRNA (from miRBase website) or other RNA (control or customer defined sequences) and a spacer segment of polyethylene glycol to extend the coding segment away from the substrate. The detection probes were made by in situ synthesis using PGR (photogenerated reagent) chemistry. The hybridization melting temperatures were balanced by chemical modifications of the detection probes. Hybridization used 100 µL 6×SSPE buffer (0.90 M NaCl, 60 mM Na$_2$HPO$_4$, 6 mM EDTA, pH 6.8) containing 25% formamide at 34° C. After RNA hybridization, tag-conjugating Cy3 and Cy5 dyes were circulated through the microfluidic chip for dye staining. Fluorescence images were collected using a laser scanner (GenePix 4000B, Molecular Device) and digitized using Array-Pro image analysis software (Media Cybernetics). Data were analyzed by first subtracting the background and then normalizing the signals using a LOWESS filter (Locally-weighted Regression) (Bolstad et al., 2003). For two color experiments, the ratio of the two sets of detected signals (log 2 transformed, balanced) and p-values of the t-test were calculated; differentially detected signals were those with p-values less than 0.01.

RT-PCR and Real-Time Analysis.

To detect the level of miRNA RT-PCR was performed using the Taqman MicroRNA reverse Transcriptase kit (Applied Biosystems, ABI) according to the manufacturer's recommendations. Five ng of RNA was used to generate cDNA with a miRNA specific primer, after which a miRNA specific Taqman probe served to detect the expression level of the miRNA of interest. Following RT-PCR with random hexamer primers (Invitrogen) on RNA samples, the expression of a subset of genes was analyzed by either PCR or quantitative real time PCR using Taqman probes purchased from ABI.

Northern Blot Analysis.

Total RNA was isolated from mouse and human cardiac tissue samples or isolated myocytes by using Trizol reagent (GibcoIBRL). Cardiac tissue samples of border zone regions of anonymous humans diagnosed as having suffered a myocardial infarction were obtained. Equal loading was confirmed by staining Northern gels with ethidium bromide. Northern blots to detect microRNAs were performed as described previously (van Rooij et al., 2006). A U6 probe served as a loading control.

Example 2

Identification of MicroRNAs that are Regulated in Human Heart Failure

To determine which miRNAs are regulated during human heat failure, RNA was isolated from both healthy heart tissue and heart tissue from patients suffering from idiopathic dilated cardiomyopathy (IDC), and a microarray for miRNAs was performed. From all 711 miRNAs measured, 31 were found to be significantly upregulated (Table 5), while 45 miRNAs were significantly downregulated (Table 6).

Among the upregulated miRNAs, several miRNAs that we previously found to be regulated during cardiac hypertrophy and remodeling in mice (e.g. miR-214, miR-21, miR-195, miR-15b, miR-199a, miR-26a and miR-23a and b) were identified. This overlap in upregulated miRNAs suggests that these miRNAs might be involved in different disease processes of the heart and actively influence the disease state. Interestingly, there are also several other miRNAs significantly induced in the diseased samples, which may actively participate in the disease (Table 5). For example, upregulation of all members of the let-7 family was observed.

TABLE 5

Upregulated miRNAs (differentially expressed transcripts p-value <0.01)

| Probe_ID | Control cardiac sample | IDC | log2 (control/IDC) | fold change |
|---|---|---|---|---|
| hsa-miR-122 | 36.48 | 33,353.67 | 9.91 | 962.1 |
| hsa-miR-34c-3p | 120.04 | 3,688.10 | 4.96 | 31.1 |
| hsa-miR-574-5p | 36.05 | 185.22 | 2.47 | 5.5 |
| hsa-miR-768-5p | 201.39 | 1,104.72 | 2.46 | 5.5 |
| hsa-miR-192 | 52.95 | 369.76 | 2.34 | 5.1 |
| hsa-miR-194 | 38.82 | 231.95 | 2.16 | 4.5 |
| hsa-miR-155 | 99.52 | 325.71 | 1.95 | 3.9 |
| hsa-miR-768-3p | 280.05 | 1,016.11 | 1.86 | 3.6 |
| hsa-miR-146b-5p | 87.28 | 338.66 | 1.63 | 3.1 |
| hsa-miR-923 | 5,664.60 | 15,261.52 | 1.45 | 2.7 |
| hsa-miR-214 | 3,017.13 | 6,445.66 | 1.10 | 2.1 |
| hsa-miR-21 | 9,352.69 | 18,911.79 | 1.05 | 2.1 |
| hsa-let-7b | 14,443.06 | 28,418.81 | 0.98 | 2.0 |
| hsa-miR-320 | 3,008.50 | 5,235.72 | 0.82 | 1.8 |
| hsa-miR-361-5p | 2,038.60 | 3,579.68 | 0.80 | 1.7 |
| hsa-miR-151-5p | 3,889.12 | 6,518.96 | 0.78 | 1.7 |
| hsa-let-7c | 21,340.60 | 36,334.98 | 0.77 | 1.7 |
| hsa-let-7f | 26,168.09 | 41,535.81 | 0.64 | 1.6 |
| hsa-let-7e | 9,971.13 | 15,426.06 | 0.64 | 1.6 |
| hsa-let-7a | 27,230.53 | 42,854.32 | 0.61 | 1.5 |
| hsa-let-7d | 20,734.80 | 31,073.26 | 0.58 | 1.5 |
| hsa-miR-92a | 4,400.94 | 6,449.08 | 0.57 | 1.5 |
| hsa-miR-423-5p | 1,428.18 | 1,971.57 | 0.52 | 1.4 |

TABLE 5-continued

Upregulated miRNAs (differentially expressed transcripts p-value <0.01)

| Probe_ID | Control cardiac sample | IDC | log2 (control/IDC) | fold change |
|---|---|---|---|---|
| hsa-miR-195 | 7,087.24 | 10,192.41 | 0.49 | 1.4 |
| hsa-let-7i | 8,125.02 | 11,287.99 | 0.48 | 1.4 |
| hsa-miR-15b | 1,803.83 | 2,508.34 | 0.43 | 1.3 |
| hsa-miR-145 | 15,652.98 | 19,878.56 | 0.38 | 1.3 |
| hsa-miR-199a-3p | 5,183.21 | 6,586.60 | 0.33 | 1.3 |
| hsa-miR-26a | 28,400.25 | 33,441.32 | 0.21 | 1.2 |
| hsa-miR-23b | 30,446.26 | 34,173.02 | 0.17 | 1.1 |
| hsa-miR-23a | 28,557.77 | 32,402.43 | 0.14 | 1.1 |

Several miRNAs that were previously found to be regulated during cardiac hypertrophy and remodeling in mice were identified among the downregulated miRNAs. For instance, all three members of the miR-29 family (miR-29a, miR-29b, and miR-29c) were downregulated in the human heart failure samples. MiR-101, which was also downregulated in the human heart failure sample, was recently confirmed to be downregulated after myocardial infarction in mice. MiR-133 and miR-1 were both downregulated in the human samples, and both of these miRNAs have been reported to be downregulated in murine models of cardiac hypertrophy and remodeling (reviewed in van Rooij et al. (2008) Trends in Genetics, Vol. 24(4): 159-166). This overlap in regulated miRNAs implies promising roles for these identified miRNAs in cardiac disease (Table 6). Interestingly, all five members of the miR-30 family (miR-30a, miR-30b, miR-30c, miR-30d, and miR-30e) were downregulated in the human heart failure samples.

TABLE 6

Downregulated miRNAs (differentially expressed transcripts p-value <0.01)

| Probe_ID | Control cardiac sample | IDC | log2 (control/IDC) | fold change |
|---|---|---|---|---|
| hsa-miR-186* | 239.29 | 19.41 | -3.62 | 12.3 |
| hsa-miR-221 | 3,710.66 | 513.54 | -2.88 | 7.4 |
| hsa-miR-223 | 545.53 | 80.34 | -2.45 | 5.5 |
| hsa-miR-424 | 275.07 | 50.70 | -2.38 | 5.2 |
| hsa-miR-19b | 423.96 | 91.17 | -2.21 | 4.6 |
| hsa-miR-422a | 930.72 | 207.10 | -2.17 | 4.5 |
| hsa-miR-148b | 160.81 | 36.01 | -2.16 | 4.5 |
| hsa-miR-22* | 508.92 | 125.15 | -2.08 | 4.2 |
| hsa-miR-365 | 323.15 | 79.34 | -2.00 | 4.0 |
| hsa-miR-30e | 4,519.51 | 1,233.35 | -1.90 | 3.7 |
| hsa-miR-29b | 2,144.01 | 585.56 | -1.90 | 3.7 |
| hsa-miR-30e* | 740.74 | 238.94 | -1.76 | 3.4 |
| hsa-miR-101 | 1,073.51 | 337.36 | -1.74 | 3.3 |
| hsa-miR-208b | 6,727.23 | 2,240.12 | -1.67 | 3.2 |
| hsa-miR-222 | 2,068.85 | 750.11 | -1.54 | 2.9 |
| hsa-miR-148a | 746.38 | 310.46 | -1.36 | 2.6 |
| hsa-miR-451 | 5,961.19 | 2,371.72 | -1.33 | 2.5 |
| hsa-miR-374b | 393.62 | 164.80 | -1.26 | 2.4 |
| hsa-miR-499-5p | 25,411.64 | 10,824.22 | -1.19 | 2.3 |
| hsa-miR-29c | 16,048.49 | 7,854.79 | -1.08 | 2.1 |
| hsa-miR-30a* | 428.86 | 198.99 | -1.04 | 2.1 |
| hsa-miR-22 | 5,618.80 | 2,819.54 | -0.99 | 2.0 |
| hsa-miR-30a | 13,199.11 | 7,102.96 | -0.99 | 2.0 |
| hsa-miR-100 | 1,844.31 | 1,000.95 | -0.94 | 1.9 |
| hsa-miR-106a | 702.52 | 347.90 | -0.93 | 1.9 |
| hsa-miR-572 | 427.56 | 227.14 | -0.91 | 1.9 |
| hsa-miR-99a | 3,069.97 | 1,599.97 | -0.83 | 1.8 |
| hsa-miR-17 | 813.93 | 458.48 | -0.80 | 1.7 |
| hsa-miR-20a | 1,107.04 | 689.68 | -0.75 | 1.7 |
| hsa-miR-27a | 17,024.56 | 10,573.08 | -0.73 | 1.7 |
| hsa-miR-29a | 16,781.16 | 10,252.74 | -0.72 | 1.6 |
| hsa-miR-143 | 16,361.00 | 9,648.78 | -0.72 | 1.6 |
| hsa-miR-30c | 17,367.39 | 10,276.92 | -0.71 | 1.6 |
| hsa-miR-30b | 20,618.98 | 12,470.91 | -0.69 | 1.6 |
| hsa-miR-133b | 20,977.84 | 13,035.90 | -0.62 | 1.5 |
| hsa-miR-30d | 10,983.35 | 7,310.62 | -0.57 | 1.5 |
| hsa-miR-125a-5p | 10,632.39 | 6,632.28 | -0.57 | 1.5 |
| hsa-miR-133a | 22,072.52 | 14,581.49 | -0.57 | 1.5 |
| hsa-miR-99b | 2,284.52 | 1,673.43 | -0.47 | 1.4 |
| hsa-miR-378 | 4,105.84 | 2,979.18 | -0.44 | 1.4 |
| hsa-miR-24 | 16,343.42 | 12,119.99 | -0.43 | 1.3 |
| hsa-miR-126 | 33,190.01 | 24,588.55 | -0.42 | 1.3 |
| hsa-miR-27b | 20,014.47 | 15,876.32 | -0.40 | 1.3 |
| hsa-miR-125b | 23,475.53 | 19,941.25 | -0.20 | 1.1 |
| hsa-miR-1 | 51,258.16 | 45,360.53 | -0.17 | 1.1 |

These data show that miRs are regulated and actively involved in the process of human heart failure. The manipulation of these identified miRNAs poses several unique opportunities for therapeutic development.

Example 3

Downregulation of miR-29 Expression after MI

Among the miRs regulated post-MI, all three members of the miR-29 family were downregulated in response to MI. This miRNA family consists of three members expressed from two bicistronic miRNA clusters. MiR-29b-1 is coexpressed with miR-29a, while the second copy of miR-29b (miR-29b-2) is co-expressed with miR-29c. All family members share a conserved seed region and miR-29a and miR-29c differ by only one base from the miR-29b sequence (FIG. 2A). Northern analysis of multiple mouse tissues indicated a comparable expression pattern for all three miR-29 family members with highest expression in the lung and liver. Of the three members, miR-29b appeared to be most prominent in the heart (FIG. 2B). By isolating cardiac myocytes and fibroblasts, the inventors found that miR-29 was expressed preferentially in the fibroblast population. The level of expression of miR-29 family members was between 5-12 fold higher in cardiac fibroblasts as compared to the expression level in cardiomyocytes that were either kept in serum free medium (SF) or stimulated with the hypertrophic agonist phenylephrine (PE) (FIG. 2C).

Northern analysis of miR-29b expression in both the borderzone of the infarcted area and the remote myocardium in four different animals verified a very consistent decrease in expression in response to MI. Compared to the baseline level and the expression in the remote myocardium, the level of miR-29b was consistently downregulated in the infarcted area three days post-MI (FIG. 2D). Real-time RT-PCR analysis further confirmed the decrease in expression of all three members of the miR-29 family within three days following MI. However, by day 14, when the infarct had healed and secondary remodeling was underway, miR-29 expression remained decreased in the region adjacent to the infarct (e.g. border zone) (FIG. 2E).

Example 4

MiR-29 Regulates the Expression of Fibrotic Genes

To begin to define the possible functions for miR-29a-c in the heart following MI, the inventors made use of computational predictions to identify possible miR-29a-c targets. The Targetscan prediction website indicated an unexpectedly high number of fibrosis-related mRNAs encoding collagens, metallopeptidases, and integrins as possible targets for miR-29a-c (word-wide web at targetscan.org). To determine whether the downregulation of miR-29a-c might regulate cardiac fibrosis, the inventors focused on predicted targets implicated in ECM production in heart. Elastin (ELN), fibrillin 1 (FBN1), collagen type I, α1 and α2 (COL1A1, COL1A2) and collagen type III, al (COL3A1) all contain one or more conserved potential seed sequences for miR-29a-c (FIG. 3A).

Because miRNAs can down-regulate the steady state levels, as well as the translation, of their target mRNAs, the inventors analyzed the expression of predicted miR-29a-c mRNA targets. Real-time RT-PCR analysis of cardiac samples 3 days after MI for these key regulatory genes for cardiac fibrosis indicated that the specific downregulation of miR-29a-c in the infarcted region correlates with the increase in expression of COL1A1, COL1A2, COL3A1, and FBN1. In contrast, ELN appeared unchanged in the border zone, and even showed an increase in the remote myocardium (FIG. 3B).

Using a CMV-driven expression plasmid, the inventors overexpressed miR-29b-1 and miR-29a in COS cells (FIG. 3C) with luciferase expression plasmids containing the 3'-UTRs of the predicted miR-29a-c targets. Increasing amounts of CMV-driven miR-29b-1/miR-29a resulted in a dose-dependent decrease in luciferase activity, while comparable amounts of miR-206, a control miRNA, had no effect (FIG. 3D). These results support the conclusion that these mRNAs are targets for repression by miR-29a-c.

Specific Methods

Cell Culture, Transfection and Luciferase Assays.

A 1793-bp genomic fragment encompassing miR-29b-1 and miR-29a coding region was amplified by PCR and ligated into pCMV6. Genomic fragments of the murine 3'UTR encompassing the miR-29 binding site(s) were PCR-amplified and ligated into the firefly luciferase (f-luc) reporter construct (pMIR-REPORT™, Ambion). COS cells were transfected with Fugene 6 (Stratagene) according to manufacturer's instructions. The total amount of DNA per well was kept constant by adding the corresponding amount of expression vector without a cDNA insert. 48 hours after transfection, cell extracts were assayed for luciferase expression using the luciferase assay kit (Promega). Relative promoter activities are expressed as luminescence relative units normalized for β-galactosidase expression in the cell extracts.

Example 5

Regulation of miR-29 in Cardiac Fibroblasts

Cardiac fibrosis is a major aspect of the remodeling process typically seen in the failing heart. The proliferation of fibroblasts and increased deposition of extracellular matrix components results in myocardial stiffness and diastolic dysfunction. Transforming growth factor β (TGFβ) has been shown to play a dominant role in the production and deposition of collagens in the heart and induces a transformation of fibroblasts into myofibroblasts (Border and Noble, 1994). Real-time PCR analysis on cardiac fibroblasts exposed to TGFβ revealed a decrease in miR-29a-c expression, suggesting that the decrease in miR-29a-c following MI might be TGFβ-regulated (FIG. 4A). Interestingly, natriuretic peptides like B-type natriuretic peptide (BNP) have been shown to inhibit TGFβ-regulated gene expression related to fibrosis and myofibroblast conversion (Kapoun et al., 2004). In this regard, the inventors reported previously that mice lacking the cardiac-specific miRNA miR-208 were resistant to cardiac fibrosis and remodeling and exhibited increased expression of BNP at baseline (van Rooij et al., 2007). Since BNP is known to antagonize the effects of TGFβ the inventors hypothesized that the increased levels of BNP in these mice might enhance the expression of miR-29a-c. Indeed, Northern analysis showed a dose-dependent increase in miR-29a-c expression upon removal of miR-208, which coincided with an increasing expression level of BNP (FIG. 4B). These data indicate that TGFβ induces the expression of collagen related genes in fibroblasts at least partly through decreasing the level of miR-29a-c, which can be inhibited by BNP secreted by cardiomyocytes.

Specific Methods

Cardiac fibroblasts (CFs) were isolated as described previously (Simpson and Savion, 1982). Briefly, hearts were excised from anesthetized neonatal 1-2 day-old Sprague-Dawley rats (Harlan Sprague Dawley, Indianapolis, Ind.), minced, and digested with pancreatin 0.1%. Cells were plated on primaria plates for 2 h, and the medium which contained the cardiomyocyte fraction of the digested tissue was removed. Cardiac fibroblasts attached and proliferated much more rapidly than cardiac myocytes; this produced virtually pure fibroblast cultures after the first passage, which was confirmed by repeated differential plating and microscopic evaluation. Cells were detached with 0.05% trypsin for passaging, and culture studies were performed at passages 2 to 4. Cells were grown in high glucose (4.5 μm/L) Dulbecco's modified Eagle's medium (DMEM) containing 10% heat-inactivated FBS and antibiotics (Penicillin and streptomycin). Myofibroblast differentiation was induced by changing the medium to low serum (2% FBS) with L-ascorbic acid (10 μg/μl) and administration of 10 ng/ml TGFβ1 for 48 hours.

Example 6

In Vivo Knockdown of miR-29 Induces Fibrosis and Expression of Collagen Genes

To further explore the potential role of miR-29a-c as a negative regulator of collagen expression, the inventors knocked down miR-29b in vivo using cholesterol-modified oligonucleotides complementary to the mature miRNA sequence of miR-29b (anti-miR-29b) and either saline or an oligonucleotide containing a four-base mismatch (mismatch miR-29b) as a negative control (FIG. 5A). Three days after a single tail vein injection of anti-miR-29b (80 mg/kg), the inventors observed a dramatic diminution of miR-29b expression in all tissues examined (FIG. 5B). In contrast, a comparable dose of the mismatch miR-29b antisense oligonucleotide had no effect on the expression level of miR-29b compared to the saline control. Knockdown by anti-miR-29b appeared to be specific to the mature miRNA, since the level of pre-miRNA remained comparable between anti-miR and mismatch-treated animals. While the knockdown in the liver and kidney appeared to be complete, a low level of miR-29b remained detectable in the heart and lung (FIG. 5B). Real-time PCR analysis indicated that miR-29b knockdown was sufficient to induce the expression of collagen genes in the liver specifically, while this effect was absent in the mismatch controls (FIG. 5C).

To enhance cardiac knockdown of miR-29b, the inventors injected 80 mg/kg of oligonucleotide intravenously on two consecutive days and collected material 3 weeks later. Northern analysis indicated complete knockdown of miR-29b in kidney and liver in response to anti-miR-29b compared to the expression level seen after injection of mismatch miR-29b (FIG. 5D). Cardiac levels of miR-29b were also dramatically reduced, while the expression of miR-29b in lung appeared unaffected by anti-miR-29b (FIG. 5D). Collagen expression in the heart was increased in response to miR-29b inhibition (FIG. 5E). Taken together, these data indicate that miR-29b functions as a negative regulator of collagen gene expression in vivo and thereby influences collagen deposition and fibrosis in the heart and liver.

Specific Methods

In Vivo miR-29b Inhibition by Synthetic Oligonucleotide Treatment.

Chemically modified oligonucleotides comprising a sequence complementary to the mature miR-29b (anti-miR-29b) were used to inhibit miR-29b activity. All nucleosides were 2'-OMe modified, the 5' terminal two and 3' terminal four bases contained a phosphorothioate internucleoside bond and the molecules contained 3' cholesterol attached via a hydroxyprolinol linker. Eight week old C57BL/6 male mice received either anti-miR-29b or mismatch miR-29b at a dose of 80 mg/kg body weight or a comparable volume of saline through tail vein injection. Tissues were collected either 3 days or 3 weeks after treatment.

Example 7

Down-Regulation of Collagen Expression with a miR-29 Mimic

To determine whether overexpression of miR-29a-c was capable of reducing collagen expression, the inventors exposed fibroblasts to a miR-29b mimic. The level of miR-29b expression in fibroblast cultures increased by as much as 400-fold after 3 days of exposure to miR-29b mimic (FIG. 5F). MiR-29a expression was unaffected and miR-29c expression was increased only slightly by the miR-29b mimic (FIG. 5F). Real-time PCR analysis indicated that the expression of collagen genes was diminished in response to the miR-29b mimic (FIG. 5G). However, the magnitude of the decrease in collagen expression was modest compared to the increase in expression of miR-29b, indicating that miR-29a-c levels are not the sole determinant of collagen levels.

Specific Methods

In Vivo miR-29b Enhancement by Synthetic Oligonucleotide Treatment.

The miR-29b mimic is a double-stranded construct consisting of guide and passenger strands. The guide strand contains T-F nucleosides at every pyrimidine residue, two 3'-terminal phosphorothioate linkages and is chemically-phosphorylated on the 5' terminus. The passenger strand contains two 5' terminal 2'-OMe residues and two 3' terminal phosphorothioate bonds. Cholesterol is attached to the 3' end of the passenger strand through a hydroxyprolinol linker. Eight week old C57BL/6 male mice received the mimic of miR-29b at a dose of 80 mg/kg body weight or a comparable volume of saline through tail vein injection. Tissues were collected either 3 days or 3 weeks after treatment.

All publications, patents and patent applications discussed and cited herein are incorporated herein by reference in their entireties. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

| Human miRNA | mature miRNA sequence | SEQ ID NO: |
|---|---|---|
| hsa-let-7a | 5'-UGAGGUAGUAGGUUGUAUAGUU-3' | 1 |
| hsa-let-7b | 5'-UGAGGUAGUAGGUUGUGUGGUU-3' | 2 |
| hsa-let-7c | 5'-UGAGGUAGUAGGUUGUAUGGUU-3' | 3 |
| hsa-let-7d | 5'-AGAGGUAGUAGGUUGCAUAGUU-3' | 4 |
| hsa-let-7e | 5'-UGAGGUAGGAGGUUGUAUAGUU-3' | 5 |
| hsa-let-7f | 5'-UGAGGUAGUAGAUUGUAUAGUU-3' | 6 |
| hsa-let-7g | 5'-UGAGGUAGUAGUUUGUACAGUU-3' | 7 |
| hsa-let-7i | 5'-UGAGGUAGUAGUUUGUGCUGUU-3' | 8 |
| hsa-miR-15b | 5'-UAGCAGCACAUCAUGGUUUACA-3' | 9 |
| hsa-miR-21 | 5'-UAGCUUAUCAGACUGAUGUUGA-3' | 10 |
| hsa-miR-199a | 5'-CCCAGUGUUCAGACUACCUGUUC-3' | 11 |
| hsa-miR-199b-5p | 5'-CCCAGUGUUUAGACUAUCUGUUC-3' | 12 |
| hsa-miR-199b-3p | 5'-ACAGUAGUCUGCACAUUGGUUA-3' | 13 |
| hsa-miR-214 | 5'-ACAGCAGGCACAGACAGGCAGU-3' | 14 |
| hsa-miR-10a | 5'-UACCCUGUAGAUCCGAAUUUGUG-3' | 15 |
| hsa-miR-10b | 5'-UACCCUGUAGAACCGAAUUUGUG-3' | 16 |
| hsa-miR-16 | 5'-UAGCAGCACGUAAAUAUUGGCG-3' | 17 |
| hsa-miR-146a | 5'-UGAGAACUGAAUUCCAUGGGUU-3' | 18 |
| hsa-miR-146b-5p | 5'-UGAGAACUGAAUUCCAUAGGCU-3' | 19 |
| hsa-miR-146b-3p | 5'-UGCCCUGUGGACUCAGUUCUGG-3' | 20 |
| hsa-miR-221 | 5'-AGCUACAUUGUCUGCUGGGUUUC-3' | 21 |
| hsa-miR-222 | 5'-AGCUACAUCUGGCUACUGGGU-3' | 22 |
| hsa-miR-497 | 5'-CAGCAGCACACUGUGGUUUGU-3' | 23 |
| hsa-miR-20a | 5'-UAAAGUGCUUAUAGUGCAGGUAG-3' | 24 |
| hsa-miR-20b | 5'-CAAAGUGCUCAUAGUGCAGGUAG-3' | 25 |
| hsa-miR-93 | 5'-CAAAGUGCUGUUCGUGCAGGUAG-3' | 26 |
| hsa-miR-101 | 5'-UACAGUACUGUGAUAACUGAA-3' | 27 |
| hsa-miR-126 | 5'-UCGUACCGUGAGUAAUAAUGCG-3' | 28 |
| hsa-miR-30a | 5'-UGUAAACAUCCUCGACUGGAAG-3' | 29 |
| hsa-miR-30b | 5'-UGUAAACAUCCUACACUCAGCU-3' | 30 |
| hsa-miR-30c | 5'-UGUAAACAUCCUACACUCUCAGC-3' | 31 |

SEQUENCE LISTING

| Human miRNA | mature miRNA sequence | SEQ ID NO: |
|---|---|---|
| hsa-miR-30d | 5'-UGUAAACAUCCCCGACUGGAAG-3' | 32 |
| hsa-miR-30e | 5'-UGUAAACAUCCUUGACUGGAAG-3' | 33 |
| hsa-miR-143 | 5'-UGAGAUGAAGCACUGUAGCUC-3' | 34 |
| hsa-miR-145 | 5'-GUCCAGUUUUCCCAGGAAUCCCU-3' | 35 |
| hsa-miR-150 | 5'-UCUCCCAACCCUUGUACCAGUG-3' | 36 |
| hsa-miR-29a | 5'-UAGCACCAUCUGAAAUCGGUUA-3' | 37 |
| hsa-miR-29b | 5'-UAGCACCAUUUGAAAUCAGUGUU-3' | 38 |
| hsa-miR-29c | 5'-UAGCACCAUUUGAAAUCGGUUA-3' | 39 |
| hsa-miR-34a | 5'-UGGCAGUGUCUUAGCUGGUUGU-3' | 40 |
| hsa-miR-34c-5p | 5'-AGGCAGUGUAGUUAGCUGAUUGC-3' | 41 |
| hsa-miR-34c-3p | 5'-AAUCACUAACCACACGGCCAGG-3' | 42 |
| hsa-miR-574-5p | 5'-UGAGUGUGUGUGUGUGAGUGUGU-3' | 43 |
| hsa-miR-574-3p | 5'-CACGCUCAUGCACACACCCACA-3' | 44 |
| hsa-miR-451 | 5'-AAACCGUUACCAUUACUGAGUU-3' | 45 |
| hsa-miR-499 | 5'-UUAAGACUUGCAGUGAUGUUU-3' | 46 |
| hsa-miR-100 | 5'-AACCCGUAGAUCCGAACUUGUG-3' | 47 |
| hsa-miR-378 | 5'-ACUGGACUUGGAGUCAGAAGG-3' | 48 |
| hsa-miR-24 | 5'-UGGCUCAGUUCAGCAGGAACAG-3' | 49 |
| hsa-miR-379 | 5'-UGGUAGACUAUGGAACGUAGG-3' | 50 |
| hsa-miR-762 | 5'-GGGGCUGGGGCCGGGGCCGAGC-3' | 51 |
| hsa-miR-335 | 5'-UCAAGAGCAAUAACGAAAAAUGU-3' | 52 |
| hsa-miR-711 | 5'-GGGACCCAGGGAGAGACGUAAG-3' | 53 |
| hsa-miR-149 | 5'-UCUGGCUCCGUGUCUUCACUCCC-3' | 54 |
| hsa-miR-218 | 5'-UUGUGCUUGAUCUAACCAUGU-3' | 55 |
| hsa-miR-181a | 5'-AACAUUCAACGCUGUCGGUGAGU-3' | 56 |
| hsa-miR-181b | 5'-AACAUUCAUUGCUGUCGGUGGGU-3' | 57 |
| hsa-miR-181c | 5'-AACAUUCAACCUGUCGGUGAGU-3' | 58 |
| hsa-miR-181d | 5'-AACAUUCAUUGUUGUCGGUGGGU-3' | 59 |
| hsa-miR-22 | 5'-AAGCUGCCAGUUGAAGAACUGU-3' | 60 |
| hsa-miR-185 | 5'-UGGAGAGAAAGGCAGUUCCUGA-3' | 61 |

REFERENCES

The following references, to the extent that they provide exemplary procedural or other details supplementary to those set forth herein, are specifically incorporated herein by reference.

U.S. Pat. No. 5,844,107
U.S. Pat. No. 5,877,302
U.S. Pat. No. 5,972,901
U.S. Pat. No. 6,008,336
U.S. Pat. No. 6,077,835
U.S. Pat. No. 6,200,801
U.S. Publn. 20020150626
U.S. Publn. 20030032615
U.S. Publn. 20030203865
U.S. Publn. 20040048787
U.S. Patent Ser. 60/952,917
U.S. Patent Ser. 60/980,303
Ambros, *Cell*, 113(6):673-676, 2003.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Baichwal and Sugden, In: *Gene Transfer*, Kucherlapati (Ed.), Plenum Press, NY, 117-148, 1986.
Banerji et al., *Cell*, 27(2 Pt 1):299-308, 1981.
Banerji et al., *Cell*, 33(3):729-740, 1983.
Barnes et al., *J. Biol. Chem.*, 272(17):11510-11517, 1997.
Benvenisty and Neshif, *Proc. Natl. Acad. Sci. USA*, 83(24): 9551-9555, 1986.
Berk et al., *Curr Opin Struct Biol.*, 17(3):302-309, 2007.
Berkhout et al., *Cell*, 59:273-282, 1989.
Bhavsar et al., *Genomics*, 35(1):11-23, 1996.
Blanar et al., *EMBO J.*, 8:1139, 1989.
Bodine and Ley, *EMBO J.*, 6:2997, 1987.
Bolstad et al., *Bioinfo.* 19, 185-193, 2003.
Border and Noble, *N. Engl. J Med.*, 331:1286-1292, 1994.
Boshart et al., *Cell*, 41:521, 1985.
Bosze et al., *EMBO j.*, 5(7):1615-1623, 1986.
Braddock et al., *Cell*, 58:269, 1989.
Brennecke et al., *Cell*, 113:25-36, 2003.
Brinster et al., *Proc. Natl. Acad. Sci. USA*, 82(13):4438-4442, 1985.
Bristow, *Cardiology*, 92:3-6, 1999.
Bulla and Siddiqui, *J. Virol.*, 62:1437, 1986.
Cai et al., *RNA*, 10(12):1957-1966, 2004.
Calin et al., *Proc. Natl. Acd. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carrington et al. *Science*, 301(5631):336-338, 2003.
Celander and Haseltine, *J. Virology*, 61:269, 1987.
Celander et al., *J. Virology*, 62:1314, 1988.
Chandler et al., *Cell*, 33:489, 1983.
Chang and Karin, *Nature*, 410(6824):37-40, 2001.
Chang et al., *Biochim. Biophys. Acta*, 1092(2):153-160, 1991.
Chang et al., *Mol. Cell. Biol.*, 9:2153, 1989.
Chang et al., *Nature*, 430(7001):785-789, 2004.
Chatterjee et al., *Proc. Natl. Acad. Sci. USA*, 86:9114, 1989.
Chen and Okayama, *Mol. Cell Biol.*, 7(8):2745-2752, 1987.
Chen et al., *Mol. Cell Endocrinol.*, 162:45-55, 2000.
Chen et al., *Science*, 303(5654):83-86, 2004.
Cheng et al., *Am. J Pathol.*, 170:1831-1840, 2007.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.

Durand et al., *Ann. Med.*, 27:311-317, 1995.
Edbrooke et al., *Mol. Cell Biol.*, 9:1908, 1989.
Edgerton and Roy, *J. Appl. Physiol.*, 89:1224-1231, 2000.
Edlund et al., *Science*, 230:912-916, 1985.
Eichhorn and Bristow, *Circulation*, 94:2285-2296, 1996.
EPO 0273085
Fabbri et al., *Proc. Natl. Acad. Sci. USA*, 104:15805-15810, 2007.
Fechheimer, et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Franz et al., *Cardioscience*, 5(4):235-43, 1994.
Friedman et al., *Genes Devel.*, 3:1314, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Gopal-Srivastava et al., *J. Mol. Cell. Biol.* 15(12):7081-7090, 1995.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36(1):59-74, 1977.
Greene et al., *Immunology Today*, 10:272, 1989
Grishok et al., *Cell*, 106:23-34, 2001.
Grosschedl and Baltimore, *Cell*, 41:885, 1985.
Grunhaus and Horwitz, *Seminar in Virology*, 3:237-252, 1992.
Harland and Weintraub, *J. Cell Biol.*, 101(3):1094-1099, 1985.
Haslinger and Karin, *Proc. Natl. Acad. Sci. USA*, 82:8572, 1985.
Hauber and Cullen, *J. Virology*, 62:673, 1988.
He et al., *Mol. Endocrinol.*, 21:2785-2794, 2007.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Natl. Acad. Sci. USA*, 90:2812-2816, 1993.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hutvagner et al., *PLoS Biol.*, 2(4):E98, 2004.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Ito and Roeder, *Trends Endocrinol. Metab.*, 12:127-134, 2001.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karlsson et al., *EMBO J.*, 5:2377-2385, 1986.
Katinka et al., *Cell*, 20:393, 1980.
Katinka et al., *Nature*, 290:720, 1981.
Kato et al, *J. Biol. Chem.*, 266:3361-3364, 1991.
Kawamoto et al., *Mol. Cell. Biol.*, 8:267, 1988.
Kelly et al., *J. Cell Biol.*, 129(2):383-396, 1995.
Kiledjian et al., *Mol. Cell. Biol.*, 8:145, 1988.
Kimura et al., *Dev. Growth Differ.* 39(3):257-265, 1997.
Kinugawa et al., *Circ. Res.*, 89:591-598, 2001.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Krenz and Robbins, *J. Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Krützfeldt et al., *Nature*, 438:685-689, 2005.
Kuhl et al., *Cell*, 50:1057, 1987.
Kunz et al., *Nucl. Acids Res.*, 17:1121, 1989.
Lagos-Quintana et al., *Science*, 294(5543):853-858, 2001.
LaPointe et al., *Hypertension* 27(3 Pt 2):715-22, 1996.
LaPointe et al., *J. Biol. Chem.*, 263(19):9075-8, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Le Gal La Salle et al., *Science*, 259:988-990, 1993.
Lee and Ambros, *Science*, 294(5543):862-864, 2001.
Lee et al., *Nature*, 294:228, 1981.
Lee et al., *Nucleic Acids Res.*, 12:4191-206, 1984.
Leung et al., *Proc. Natl. Acad. Sci. USA*, 48:18125-18130, 2006.
Levinson et al., *Nature*, 295:79, 1982.
Levrero et al., *Gene*, 101:195-202, 1991.
Lijnen et al., *Mol. Genet. Metab.*, 71:418-435, 2000.
Lin et al., *Mol. Cell. Biol.*, 10:850, 1990.
Liu et al., *Proc Natl Acad Sci USA* 101:9740-9744, 2004.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Majors and Vannus, *Proc. Natl. Acad. Sci. USA*, 80:5866, 1983.
Mann et al., *Cell*, 33:153-159, 1983.
Mansen et al., *Mol. Endocrinol.*, 15:2106-2114, 2001.
Markowitz et al., *J. Virol.*, 62:1120-1124, 1988.
McNeall et al., *Gene*, 76:81, 1989.
Meister and Tuschl, *Nature*, 431:343-9, 2004.

Miksicek et al., *Cell*, 46:203, 1986.
Molkentin et al., *Cell* 93:215-228, 1998.
Mordacq and Linzer, *Genes and Dev.*, 3:760, 1989.
Moreau et al., *Nucl. Acids Res.*, 9:6047, 1981.
Morkin, *Microsc. Res. Tech.*, 50:522-531, 2000.
Moss et al., *Biol. Chem.*, 271(49):31688-31694, 1996.
Muesing et al., *Cell*, 48:691, 1987.
Mujumdar and Tyagi, *J Hypertens*, 17:261-270, 1999.
Naya et al., *J Biol Chem*, 275(7):4545-4548, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ojamaa et al., *Endocrinology*, 141:2139-2144, 2000.
Ondek et al., *EMBO J.*, 6:1017, 1987.
Ornitz et al., *Mol. Cell. Biol.*, 7:3466, 1987.
Palmiter et al., *Nature*, 300:611, 1982.
Paskind et al., *Virology*, 67:242-248, 1975.
Pasquinelli and Ruvkun, *Ann. Rev. Cell Dev. Biol.*, 18:495-513, 2002.
PCT Appln. WO 0071096
PCT Appln. WO 84/03564
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al., *Genes and Dev.*, 2:1144, 1988.
Sambrook and Russell, Molecular Cloning: A Laboratory Manual 3$^{rd}$ Ed., Cold Spring Harbor Laboratory Press, 2001.
Satake et al., *J. Virology*, 62:970, 1988.
Sayed et al., *Circ. Res.*, 100:416-424, 2007.
Schaffner et al., *J. Mol. Biol.*, 201:81, 1988.
Schuyler and Yarbrough, *Basic Res. Cardiol.*, 85:481-494, 1990.
Searle et al., *Mol. Cell. Biol.*, 5:1480, 1985.
Sempere et al., *Genome Biol* 5:R13, 2004.
Sengupta et al., *Proc. Natl. Acad. Sci. USA*, 105(15):5874-5878, 2008.
Shelton et al., *J Lipid Res.*, 41:532-537, 2000.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shingara et al., *RNA* 11:1461-1470, 2005.
Simpson and Savion, *Circ. Res.*, 50:101-116, 1982.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
The Merck Index, Eleventh Edition
Thiesen et al., *J. Virology*, 62:614, 1988.
Top et al., *J. Infect. Dis.*, 124:155-160, 1971.
Treisman, *Cell*, 46(4):567-174, 1986
Tronche et al., *Mol. Biol. Med.*, 7:173, 1990.
Tronche et al., *Mol. Cell Biol.*, 9(11):4759-4766, 1989.
Trudel and Constantini, *Genes and Dev.*, 6:954, 1987.
Tur-Kaspa et al., *Mol. Cell Biol.*, 6:716-718, 1986.
Tyndell et al., *Nuc. Acids. Res.*, 9:6231, 1981.
van Rooij et al., *Science*, 316:575-579, 2007.
van Rooij et al., *Proc. Natl. Acad. Sci. USA*, 103(48):18255-18260, 2006.
Vannice and Levinson, *J. Virology*, 62:1305, 1988.
Varmus et al., *Cell*, 25:23-36, 1981.
Vasseur et al., *Proc Natl. Acad. Sci. USA*, 77:1068, 1980.
Wagner et al., *Proc. Natl. Acad. Sci. USA* 87(9):3410-3414, 1990.
Wang and Calame, *Cell*, 47:241, 1986.
Weber et al., *Cell*, 36:983, 1984.
Wei et al., *J. Endocrinol. Invest.*, 28:8-11, 2005.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Xu et al., *Curr. Biol.*, 13:790-795, 2003.
Yamauchi-Takihara, et. al., *Proc. Natl. Acad. Sci. USA*, 86(10):3504-3508, 1989.
Yang and Russell, *Proc. Natl. Acad. Sci. USA*, 87:4144-4148, 1990.
Yao and Eghbali, *Circ. Res.* 71:831-839, 1992.
Young et al., In: *Handbook of Applied Therapeutics*, 7.1-7.12 and 9.1-9.10, 1989. Yutzey et al., *Mol. Cell. Biol.*, 9:1397, 1989.
Zelenin et al., *FEBS Lett.*, 287(1-2):118-120, 1991.
Zeng et al., *Cancer Res.*, 62(13):3630-3635, 2002.
Zhao et al., *Nature*, 436:214-220, 2005.
Ziober and Kramer, *J. Bio. Chem.*, 271(37):22915-22, 1996.

The invention claimed is:

1. A method of treating myocardial infarction in a subject in need thereof comprising administering to the heart or coronary vasculature of the subject an inhibitor of miR-146a or miR-146b, wherein the inhibitor is an antisense oligonucleotide or an antagomir, and wherein one or more symptoms of myocardial infraction is improved in the subject following administration of the inhibitor.

2. The method of claim 1, wherein the antisense oligonucleotide or antagomir comprises a sequence that is at least partially complementary to a mature sequence of miR-146a or miR-146b.

3. The method of claim 1, wherein the antisense oligonucleotide comprises at least one sugar and/or backbone modification.

4. The method of claim 1, wherein the antisense oligonucleotide is about 8 to about 18 nucleotides in length.

5. The method of claim 1, wherein the inhibitor is administered to the subject by intravenous administration or direction injection into cardiac tissue.

6. The method of claim 1, further comprising administering to the subject a second cardiac therapy.

7. The method of claim 6, wherein the second cardiac therapy is selected from the group consisting of a β blocker, an ionotrope, a diuretic, ACE-I, AII antagonist, BNP, a $Ca^{++}$-blocker, an endothelin receptor antagonist, or an HDAC inhibitor.

8. The method of claim 1, wherein fibrosis in the infarct zone is reduced following administration of the inhibitor.

9. The method of claim 1, wherein apoptosis of heart cells in the infarct zone is reduced following administration of the inhibitor.

10. The method of claim 1, wherein the subject is a human.

11. The method of claim 2, wherein the antisense oligonucleotide or antagomir comprises a sequence that it at least partially complementary to the sequence of SEQ ID NO: 18 or SEQ ID NO: 19.

12. The method of claim 11, wherein the antisense oligonucleotide or antagomir comprises a sequence that it fully partially complementary to the sequence of SEQ ID NO: 18 or SEQ ID NO: 19.

13. The method of claim 3, wherein the sugar modification is a bicyclic sugar nucleoside modification, a 2'-O-alkyl modification, or a 2'-fluoro modification.

14. The method of claim 13, wherein the bicyclic sugar nucleoside modification is a locked nucleic acid.

15. The method of claim 2, wherein the backbone modification is a phosphorothioate linkage.

16. The method of claim 1, wherein the antisense oligonucleotide is about 12 to about 16 nucleotides in length.

17. The method of claim 10, wherein the human is suffering from idiopathic dilated cardiomyopathy.

* * * * *

UNITED STATES PATENT AND TRADEMARK OFFICE
CERTIFICATE OF CORRECTION

PATENT NO. : 9,072,765 B2  
APPLICATION NO. : 13/321756  
DATED : July 7, 2015  
INVENTOR(S) : Eric N. Olson and Eva van Rooij Page 1 of 1

It is certified that error appears in the above-identified patent and that said Letters Patent is hereby corrected as shown below:

In the specification

In column 1, line 17, delete "grant support" and insert --government support-- therefor.

In the claims

In claim 7, column 59, line 59, delete "All antagonist" and insert --AII antagonist-- therefor.

In claim 15, column 60, line 55, delete "claim 2" and insert --claim 3-- therefor.

Signed and Sealed this
Fifteenth Day of December, 2015

Michelle K. Lee
*Director of the United States Patent and Trademark Office*